United States Patent [19]

Newton

[11] Patent Number: 5,420,099
[45] Date of Patent: May 30, 1995

[54] SULFANOMIDE HERBICIDES

[75] Inventor: Trevor W. Newton, Schwabenheim, Germany

[73] Assignee: Shell Research Limited, London, United Kingdom

[21] Appl. No.: 994,400

[22] Filed: Dec. 21, 1992

[30] Foreign Application Priority Data

Dec. 24, 1991 [EP] European Pat. Off. ............ 91122208

[51] Int. Cl.$^6$ ............... C07D 239/34; C07D 239/46; C07D 239/60; C07D 401/12; C07D 403/12; C07D 413/12; A01N 43/54

[52] U.S. Cl. ............... 504/242; 504/191; 504/221; 504/222; 504/223; 504/225; 504/230; 504/237; 504/243; 544/3; 544/4; 544/8; 544/54; 544/58.6; 544/60; 544/64; 544/66; 544/67; 544/82; 544/96; 544/112; 544/113; 544/120; 544/121; 544/123; 544/83; 544/295; 544/296; 544/181; 544/182; 544/212; 544/216; 544/225; 544/238; 544/300; 544/301; 544/310; 544/311; 544/312; 544/316; 544/317

[58] Field of Search ............... 504/242, 243, 191, 223, 504/237; 544/295, 296, 300, 301, 312, 238, 212, 83, 120, 96, 66, 58.6

[56] References Cited

U.S. PATENT DOCUMENTS 5,062,882 11/1991 Newton et al.
5,158,599 10/1992 Astles .................. 504/242

FOREIGN PATENT DOCUMENTS 03193765 9/1991 Japan.
03200772 9/1991 Japan.

*Primary Examiner*—John M. Ford
*Attorney, Agent, or Firm*—Peggy Ann Climenson

[57] ABSTRACT

A compound having the formula

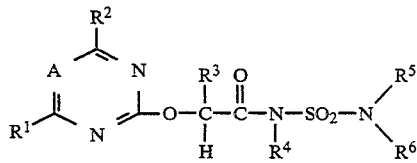

wherein A is $CR_7$; and $R^1$ through $R^7$ are substituents such as hydrogen, halogen, branched and straight chain hydrocarbons, cyclic hydrocarbons, aromatics, and sulfur and nitrogen containing functional groups. Further, $R^5$ and $R^6$ may be taken together with the atom to which they are attached to form a group

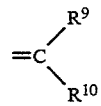

in which $R^9$ and $R^{10}$ are further functional groups. The compounds are useful in herbicidal compositions, particularly in combination with carriers and surfactants. A process for making this compound is also presented.

13 Claims, No Drawings

SULFANOMIDE HERBICIDES

FIELD OF THE INVENTION

The present invention relates to certain new sulfonamide derivatives, their preparation, herbicidal compositions containing them and their use in combating undesired plant growth.

BACKGROUND OF THE INVENTION

Sulfonamide compounds are well known for their biological activity. Certain classes of sulfonamide derivatives are useful as herbicides while other classes are useful as anti-bacterial agents.

In EP-A-0411706 it is disclosed that sulfonamide compounds of the general formula

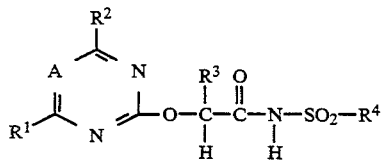

in which A is a nitrogen atom or a group $CR^5$, each of $R^1$, $R^2$, $R^3$, and $R^5$ is one of a range of moieties, and $R^4$ is an optionally substituted alkyl, aralkyl, aryl or heterocyclic group, or salts thereof, exhibit herbicidal activity.

A class of sulfanomide derivatives has now been found which differ structurally from those disclosed in EP-A-0411706 in that the terminal group $R^4$ has been replaced by a substituted amino group and which have useful herbicidal properties.

SUMMARY OF THE INVENTION

The present invention thus provides a compound of the general formula

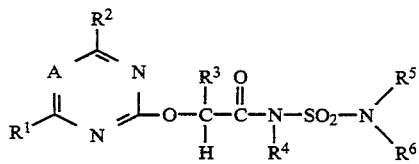

(I)

in which A is a nitrogen atom or $CR^7$;

$R^1$, $R^2$ and $R^7$ each independently are hydrogen halogen formyl, cyano, carboxy or azido, or optionally substituted alkyl alkenyl, alkynyl, cycloalkyl, alkoxy, alkenyloxy, alkynyloxy, aryloxy, alkylthio, alkenylthio, alkynylthio, arylthio, alkylcarbonyl, alkoxycarbonyl, amino, aminoxy, or dialkylaminoxy;

$R^3$ is hydrogen, or optionally substituted alkyl, alkenyl, alkynyl, cycloalkyl, heterocyclic, aralkyl or aryl;

$R^4$ is hydrogen, or optionally substituted alkyl, alkenyl, aralkyl, aryl or heterocyclic group, or optionally substituted acyl group of the formula $COR^8$ in which $R^8$ is alkyl, aryl or aralkyl; and $R^5$ and $R^6$ each independently are hydrogen, or optionally substituted alkyl, alkoxy, alkenyl, akynyl, aryl, aralkyl, amino, cycloalkyl, or heterocyclic group, or a group of the formula $-SO_2R^8$, in which $R^8$ is defined above, or

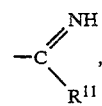

in which $R^{11}$ is an alkylthio group, or $R^5$ and $R^6$ together form a group

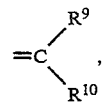

in which $R^9$ and $R^{10}$ independently are hydrogen, or alkyl, alkoxy, aryl, aralkyl or dialkylamino, or $R^9$ and $R^{10}$ together form an optionally substituted heterocyclic group, or $R^5$ and $R^6$ together form an alkylene chain which is optionally interrupted by an oxygen, sulphur, or —NR— in which R is hydrogen or alkyl or a salt thereof.

Each alkyl, alkenyl, or alkynyl independently is a straight or branched chain group. Preferably each alkyl has from 1 to 12 carbon atoms, more preferably from 1 to 6 carbon atoms, and especially from 1 to 4 carbon atoms. Alkenyl or alkynyl groups have from 2 to 12 carbon atoms, preferably from 2 to 6 carbon atoms and especially from 2 to 4 carbon atoms. Cycloalkyl groups have from 3 to 8 carbon atom ring members.

Each aryl is a single fused or carbocyclic ring system having from 6 to 10 ring members. Preferably an aryl radical or moiety comprises a single ring system and preferably is a phenyl ring.

A heterocyclic radical is a single or fused, saturated or unsaturated, ring system having from 5 to 10 ring members preferably 5 or 6 ring members of which from 1 to 3 ring members are hetero atoms selected from oxygen, nitrogen and sulphur atoms.

Radicals represented by the symbols $R^1$, $R^2$, $R^3$, $R^4$, $R^5$, $R^6$, $R^7$, $R^8$, $R^9$, $R^{10}$ are unsubstituted or substituted. Where substituents are present, the substituent groups are any of those customarily employed in the modification and/or development of pesticidal compounds and are especially substituents that maintain or enhance the herbicidal activity associated with the compounds of the present invention, or influence persistence of action soil or plant penetration, or any other desirable property for herbicidal compounds. There may be one or more of the same or different substituents present in each radical.

Substituents for alkyl, alkenyl, alkynyl, alkoxy, alkenyloxy, alkynyloxy, alkylthio, alkenylthio, alkylcarbonyl and alkoxycarbonyl or alkyl moieties in aralkyl groups are independently selected from halogen, alkoxy, alkenyloxy, aryloxy, hydroxy, alkylthio, arylthio, aryl, alkylsulfonyl, alkylsulfinyl, alkylenedioxy, alkylenedithio, haloalkyl, and alkoxycarbonyl groups, heterocyclic groups, dialkyliminoxy, optionally substituted amino, trialkylsilyl, alkylcarbonyl, arylcarbonyl, alkoxycarbonyl, carboxy, cyano, thiocyanato, or optionally substituted aminocarbonyl groups.

Substituents for aryl, cycloalkyl aryloxy or arylthio groups, heterocyclic rings or aryl moieties in aralkyl groups are independently selected from halogen, nitro, cyano, alkyl, haloalkyl alkoxy, haloalkoxy, alkylthio, alkylsufonyl, mono- or di-alkylsulfonamido, aryloxy, carboxy, alkoxycarbonyl or aralkoxycarbonyl groups.

Substituents for amino groups are independently selected from alkyl, alkenyl, aryl, alkoxy, amino, mono- or di-alkylamino, arylamino, alkoxyalkyl, haloalkyl, hydroxy, hydroxyalkyl, cyano, carboxyalkyl or alkylcarbonylamino, or the amino group may form part of a heterocyclic ring.

Suitable salts of the invention are agrochemically acceptable salts of compounds of general formula I. Salts are formed with inorganic or organic cations by conventional methods. Such salts suitably include salts with inorganic cations derived from alkali metals and alkaline earth metals such as, for example, sodium, potassium, calcium and magnesium, and from transition metals, for example copper, or salts with organic cations such as alkylammonium and alkylsulfonium cations.

A haloalkyl has from 1 to 3 halogen atoms. Halogen as a substituent is suitably fluorine, chlorine or bromine. A preferred haloalkyl radical is trifluoroethyl.

A is preferably nitrogen or CH.

Suitable examples of the radical $R^1$ include $C_{1-4}$ alkyl, $C_{1-4}$ alkoxy, and $C_{1-4}$ haloalkyl, preferably methyl, methoxy and trifluoromethyl groups. Suitable examples of the radical $R^2$ include $C_{1-4}$ alkyl, $C_{1-4}$ alkoxy and halogen, preferably methyl, methoxy or chlorine.

Suitable examples of the radical $R^3$ include $C_{1-6}$ alkyl and phenyl. Preferably the radical $R^3$ is selected from methyl, ethyl, n-propyl, n-butyl, i-butyl, s-butyl, t-butyl or phenyl.

Preferably, $R^4$ is hydrogen.

Suitably, $R^5$ and $R^6$ independently are hydrogen, $C_{1-6}$ alkyl, $C_{1-6}$ haloalkyl, $C_{1-6}$ alkoxy, $C_{2-6}$ alkenyl, $C_{2-6}$ alkynyl, mono- or di-($C_{1-6}$ alkoxy)$C_{1-4}$ alkyl, ($C_{1-4}$ alkoxy) carbonyl ($C_{1-4}$ alkyl), $C_{3-8}$ cycloalkyl or benzyl, or optionally substituted phenyl, pyridyl, pyrimidinyl, or ($C_{3-8}$ cycloalkyl)$C_{1-4}$ alkyl, or a group

in which $R^{11}$ is a $C_{1-4}$ alkylthio or $R^5$ and $R^6$ together form a group

in which $R^9$ and $R^{10}$ independently are $C_{1-4}$ alkyl, $C_{1-4}$ alkoxy or di($C_{1-4}$ alkyl)amino or and $R^9$ and $R^{10}$ together form a five-membered ring in which two or three ring members are hetero atoms selected from nitrogen or sulphur atoms, the ring being substituted by a benzyl or one or two $C_{1-4}$ alkyl groups, or $R^5$ and $R^6$ together form an alkylene chain which is optionally interrupted by oxygen or —NR— in which R is $C_{1-4}$ alkyl.

Preferably $R^5$ is hydrogen or methyl or ethyl, $R^6$ is hydrogen, methyl, ethyl, n-propyl, i-propyl, n-butyl, methoxy, chloroethyl, methoxycarbonylmethyl, mono- or di- methoxyethyl, allyl, propynyl, cyclopropyl, cyclobutyl, pyridyl, dimethylprimidinyl, (dichlorocyclopropyl)methyl, phenyl, chlorophenyl, benzyl or the group

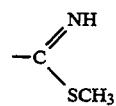

or $R^5$ and $R^6$ together represent one of the groups

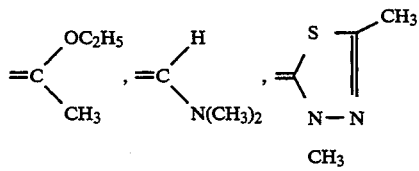

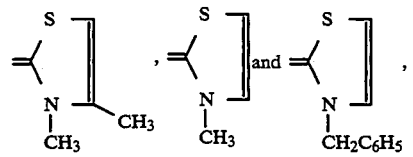

together are —(CH$_2$)$_2$O(CH$_2$)$_2$—, —(CH$_2$)$_2$N(CH$_3$)(CH$_2$)$_2$— or —(CH$_2$)$_4$—.

It will be appreciated that the compounds of the present invention in which $R^3$ is other than a hydrogen atom have an asymmetric carbon atom and will therefore exist in different stereoisomeric forms. The present invention accordingly includes all individual isomeric forms of the compounds of general formula I and mixtures thereof in whatever proportion. Thus, the R- and S-enantiomers of the compound of general formula IA

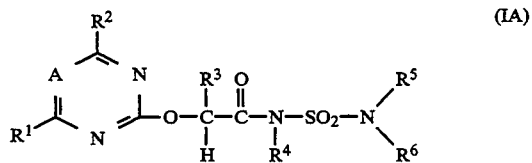

in which A, $R^1$, $R^2$, $R^4$, $R^5$ and $R^6$ are as hereinbefore defined and $R^3$ is other than hydrogen, and mixtures thereof, are included within the present invention.

In accordance with the present invention there is also provided a process for the preparation of a compound of the general formula I, which process comprises (a) reacting a compound of the general formula II

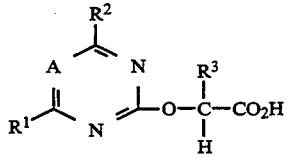

in which A, $R^1$, $R^2$, $R^3$ are as defined above, or the corresponding ester, acid chloride or acid anhydride, with a compound of the general formula

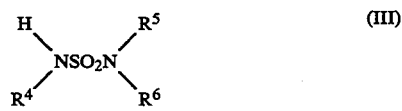

in which $R^4$, $R^5$ and $R^6$ are as previously defined or a salt thereof or, in an alternate embodiment, (b) reacting a compound of the general formula

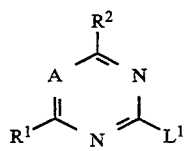

in which A, $R^1$ and $R^2$ are as previously defined and $L^1$ represents a leaving group, with a di-salt when $R^4$ is hydrogen, and a mono-salt when $R^4$ represents a moiety other than hydrogen, of the compound of the general formula

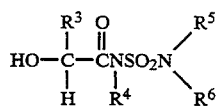

in which $R^3$, $R^4$, $R^5$ and $R^6$ are as previously defined.

The leaving group is any group that will, under the reaction conditions, cleave from the starting material thus promoting reaction at a specified site. The leaving group $L^1$ is suitably halogen, for example, bromine, chlorine or iodine, or alkanesulfonyl, for example, methanesulfonyl.

The salt of compound V is suitably an alkali metal salt, preferably a sodium salt.

Process (a) is suitably carried out at ambient or elevated temperature, i.e., at a temperature above 20° C. A preferred temperature range in which to carry out the reaction is from about 20° C. to about 80° C. An especially suitable reaction temperature is from about 20° C. to about 50° C. The molar ratio of reactant II to reactant III is from about 1.0 to about 5.0, preferably about from 1.0 to about 2.5.

The reaction (a) is carried out in an inert organic solvent such as a hydrocarbon covalent, e.g., benzene or toluene, a chlorinated hydrocarbon, e.g., dichloromethane or chloroform, an alcohol, e.g., methanol or ethanol, an ether, e.g., diethyl ether, tetrahydrofuran, 1,4-dioxane, a ketone, e.g., acetone or methyl ethyl ketone, an ester e.g., ethyl acetate, an aprotic polar solvent, e.g., dimethylformamide, dimethylacetamide or dimethylsulfoxide or a nitrile, e.g., acetonitrile.

Preferably, the reaction (a) is carried out in the presence of a tertiary amine, for example, 1,8-diazabicyclo[5.4.0]undec-7-ene. Other suitable tertiary amines include triethylamine and pyridine.

When the reactant II is in the form of a free carboxylic acid, the carboxy group is preferably activated for the reaction to proceed by the presence of a carbonyl-activating agent. Suitable carboxyl-activating agents include 2-chloro-N-methyl pyridinium iodide, dicyclohexylcarbodiimide and carbonyldiimidazole. Suitably the acid reactant II is activated by the carboxyl-activating agent in the presence of an inert organic solvent at ambient or elevated temperature from about 20° C. to the reflux temperature of the mixture, prior to the addition of reactant III, and if desired, the tertiary amine.

Process (b) is suitably carried out at a temperature from about ambient to the reflux temperature of the reaction medium, preferably from about 100° C. to about 150° C., for example at 120° C. The molar ratio of the reactants IV:V is suitably from about 1.0 to about 2.5.

In reaction (b) the salt is suitably prepared from a compound V by the action of an alkali metal, such as metallic sodium or potassium, or conveniently, a strong base, for example, an alkali metal hydride, such as sodium or potassium hydride, an alkaline earth metal hydride, such as calcium hydride, an alkali metal alkoxide, such as sodium or potassium hydroxide. Suitably conversion of a hydroxy compound V to the salt occurs in situ.

The reaction (b) is carried out in the presence of a solvent. Typical solvents are the same as those solvents noted above for process (a).

The compound of general formula I is converted to other compounds of general formula I by methods known to the art, provided that suitable care is taken to ensure that the sulfonamide group is not affected. Thus for example, a compound of general formula I where $R^1$ and/or $R^2$ represents a halogen atom, particularly chlorine, is transformed into other derivatives by nucleophilic displacement, for example by reaction with two equivalents of an amine, such as dimethylamine, to give the corresponding compound of general formula I in which $R^1$ and/or $R^2$ represents a substituted amino group. Likewise a compound of general formula I in which $R^1$ and/or $R^2$ represents a halogen atom, is reacted with two equivalents of alkylthio organo-metallic compound, for example sodium methanethiolate, to yield the corresponding compound of general formula I in which $R^1$ and/or $R^2$ is a hydrogen atoms. Furthermore, a compound of general formula I in which $R^4$ represents hydrogen is converted by known methods into the corresponding compound of formula I in which $R^4$ represents a moiety other than a hydrogen atom.

Individual enantiomers are obtained using stereospecific reactants or by conventional resolution techniques.

The prepared compounds of the invention are, if desired, isolated and purified using conventional techniques.

Suitable starting carboxylic acids of general formula II, and esters thereof, and also their preparation, are described and claimed in EP-A-0400741. Thus, the starting carboxylic acids of general formula II, and esters thereof, are prepared either by reacting a compound of the general formula

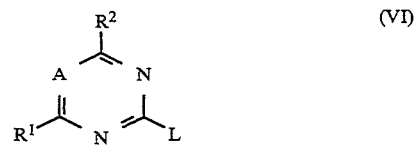

in which $R^1$, $R^2$ and A are defined above and L is a leaving group, for example, a halogen atom or alkanesulfonyl group, with a compound of the general formula

in which $R^3$ is as defined above, or an ester thereof, or for compounds in which A represents $CR^7$, reacting a compound of the general formula

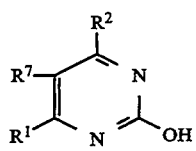

in which R¹, R² and R⁷ are as defined above with an ester of a compound of the general formula

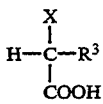

in which R³ is as defined above and X is a leaving group such as a halogen atom or a sulfonyloxy group. The acid chloride and acid anhydride derivatives are prepared from the compounds of formula II by standard techniques.

The reactants of general formula III are either known or are prepared using techniques described in the literature. For example, the compounds are prepared by methods such as those described in (A) G. Lohaus, Chem, Ber., 105, 2791 (1972) or in (B) G. Weiss and G. Schulze, Liebigs Ann. Chem., 729, 40 (1969).

The starting triazine compounds of general formulae IV and VI (i.e., in which A is nitrogen atom) are either known or are prepared using techniques described in the literature. For example, such compounds are prepared from 2,4,6-trichlorotriazine, by methods such as those described by Dudley et al, J. Am. Chem. Soc., 73, 2986 (1951); Koopman et al, Rec. Trav. Chim., 79, 83 (1960); Hirt et al, Helv. Chim. Acta, 33, 1365 (1950); Kobe et al, Monatshefte fur Chemie, 101, 724 (1970) and Ross et al, U.S. Pat. Specification No. 3,316,263.

The starting pyrimidines of general formulae IV, VI and VIII (i.e., in which A is a group CH) are prepared by conventional techniques, for example those described in Heterocyclic compounds, 16, "The Pyrimidines", edited by D. J. Brown, Interscience, 1962.

The compounds of general formula V are prepared from the corresponding benzyloxy derivatives

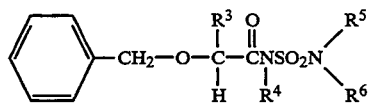

by hydrogenation using gaseous hydrogen in conjunction with a palladium- or platinum-carbon catalyst. The benzyloxy derivatives are prepared in analogous fashion for reaction (a) above by the reaction of an appropriate 2-benzyloxycarboxylic acid

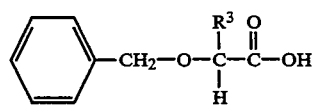

or reactive derivative thereof, with a compound of general formula III described above, or a salt thereof.

The compounds of general formula VII are either known compounds or are prepared by conventional procedures. Compounds in which R³ represents an aryl group are prepared by treating the corresponding aldehyde, R³CHO, with a suitable cyanide compound, for example, potassium cyanide or trimethylsilylcyanide, with, respectively, zinc iodide or sodium bisulfite, followed by conversion of the cyano substituent to the acid group. See, for example, Schnur and Morville, J. Med. Chem. 29, 770 (1986) and U.S. Pat. Specification No. 4,537,623. Compounds in which R³ represents an alkyl group are, for example, prepared by the method of Kolasa and Miller, J. Org. Chem 52, 4978 (1987), starting from a suitable amino acid with a two stage conversion.

The compounds of general formula I have been found to have useful herbicidal activity. Accordingly, the present invention further provides a herbicidal composition comprising a compound of formula I as defined above in association with at least one carrier.

A carrier in a composition according to the invention is any material with which the active ingredient is formulated to facilitate application to the locus to be treated, which is for example, a plant, seed or soil, or to facilitate storage, transport or handling. A carrier is usefully a solid or a liquid, including a material which is normally gaseous but which has been compressed to form a liquid, and any of the carriers normally used in formulation herbicidal compositions may be used. Preferably compositions according to the invention contain 0.5% to 95% by weight of active ingredient.

Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example kaolinites, montmorillonites and micas; calcium carbonate; calcium sulfate; ammonium sulfate; synthetic hydrated silicon oxides and synthetic calcium or aluminum silicates; elements, for example, carbon and sulfur; natural and synthetic resins, for example, coumarone resins, polyvinyl chloride, and styrene polymers and copolymers; solid polychlorophenols; bitumen; waxes; and solid fertilizers, for example, superphosphates.

Suitable liquid carriers include water; alcohols, for example, isopropanol and glycols; ketones, for example, acetone, methyl ethyl ketone, methyl isobutylketone and cyclohexanone; ethers; aromatic or araliphatic hydrocarbons, for example, benzene toluene and xylene; petroleum fractions, for example, kerosine and light mineral oils; chlorinated hydrocarbons, for example, carbon tetrachloride, perchloroethylene and trichloroethane. Mixtures of different liquids are often suitable.

Agricultural compositions are often formulated and transported in a concentrated form which is subsequently diluted by the user before application. The present of small amounts of a carrier which is also a surface active agent facilitates this process of dilution. Thus preferably at least one carrier in a composition according to the invention is a surface-active agent. For example, the composition usefully contains at least two carriers, at least one of which is a surface-active agent.

A surface-active agent is an emulsifying agent, a dispersing agent or wetting agent. It is nonionic or ionic. Examples of suitable surface-active agents include the sodium or calcium salts of polyacrylic acids and lignin sulfonic acids; The condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example sodium lauryl sulfate, sodium secondary alkyl sulfates, sodium salts of sulfonated castor oil, and sodium alkylaryl sulfonates such as dodecylbenzene sulfonate; and polymers of ethylene oxide and copolymers of ethylene oxide and propylene oxide.

The compositions of the invention are formulated as wettable powders, dusts, granules, solutions, emulsifiable concentrates, emulsions, suspension concentrates and aerosols. Wettable powders usually contain 25%, 50% or 75% wt of active ingredient and usually contain in addition to solid inert carrier, 3%–10% wt of a dispersing agent and, where necessary, 0–10% wt of stabilizer(s) and/or other additives such as penetrants. Dusts are usually formulated as a dust concentrate having a similar composition to that of a wettable powder but without a dispersant, and are diluted in the field with further solid carrier to give a composition usually containing 0.5%–10% wt of active ingredient. Granules are usually prepared to have a size between 10 BS mesh and 100 BS mesh (1.676 mm–0.152 mm), and are manufactured by agglomeration or impregnation techniques. Generally, granules will contain 0.5%–75% wt active ingredient and 0–10% wt of additives such as stabilizers surfactants, slow release modifiers and binding agents. The so-called "dryflowable powders" consist of relatively small granules having a relatively high concentration of active ingredient. Emulsifiable concentrates usually contain, in addition to a solvent and, when necessary, co-solvent, 10%–50% wt/v active ingredient, 2%–20% wt/v emulsifiers and 0–20% wt/v of other additives such as stabilizers, penetrants and corrosion inhibitors. Suspension concentrates are usually compounded so as to obtain a stable, non-sedimenting flowable product and usually contain 10%–75% wt active ingredient, 0.5%–15% wt of dispersing agents, 0.1%–10% wt of suspending agents such as protecting colloids and thixotropic agents, 0–10% wt of other additives such as defoamers, corrosion inhibitors, stabilizers and penetrants, and water or an organic liquid in which the active ingredient is substantially insoluble. Certain organic solids or inorganic salts are present dissolved in the formulation to assist in preventing sedimentation or as anti-freeze agents for water.

Aqueous dispersions and emulsions, for example, compositions obtained by diluting a wettable powder or a concentrate according to the invention with water, also are within the scope of the invention. The said emulsions are of the water-in-oil or of the oil-in-water type, and have a thick 'mayonnaise'-like consistency.

The composition of the invention may also contain other active ingredients, for example, compounds possessing insecticidal or fungicidal properties or other herbicides.

The present invention still further provides the use as a herbicide of a compound of the general formula I as defined above or a composition as defined above and a method of combating undesired plant growth at a locus with such a compound or composition according to the present invention. The locus may, for example, be the soil or plants in a crop area. The dosage of active ingredient used is from 0.01 kg/ha to 10 kg/ha, suitably 0.05 kg/ha to 4 kg/ha.

Examples 1–166 below illustrate the process of the present invention. Examples 1 and 2 illustrate the preparation of intermediates of general formula III, by Methods (a) and (b) respectively, while Examples 3 to 166 illustrate compounds of general formula I.

EXAMPLE 1

Preparation of 1-n-butylsulfamide (i) A solution of chlorosulfonylisocyanate (60.9 g, 0.43 mol) in toluene (20 ml) was added dropwise to a stirred solution of 2,4,5-trichlorophenol (84.9 g, 0.43 mol) in toluene (80 ml), while maintaining the temperature of the reaction mixture at or below 35° C. After the addition was complete, the mixture was refluxed for 3 hours, during which time copious amounts of hydrogen chloride were evolved. The mixture was then cooled to 40° C. and water was added dropwise until no further carbon dioxide was evolved. The white precipitate which formed was collected by filtration and dried to give the crude O-(2,4,5-trichlorophenyl)-sulfamate as white crystals (93.0 g, 78%), m.p. 153°–155° C., which was used without further purification.

(ii) O-(2,4,5-trichlorophenyl)-sulfamate (13.83 g, 50 mmol) was added in two portions to a stirred solution of n-butylamine (4.94 ml, 50 mmol) and triethylamine (6.9 ml, 50 mmol) in acetonitrile (50 ml). After stirring for 5 min, the solution was evaporated in vacuo. The residue was dissolved in ethyl acetate (50 ml) and the organic phase was washed with 0.05N hydrochloric acid (2×25 ml). The organic phase was then dried (sodium sulfate) and evaporated in vacuo. The residue was purified by flash chromatography (ethyl acetate/petroleum ether, 40:60, followed by pure ethyl acetate) to give the 1-n-butylsulfamide as a pale brown waxy solid (2.52 g, 33%).

EXAMPLE 2

Preparation of 1-methylsulfamide (i) Sulfuryl chloride (81.3 ml, 1.0 mol) and antimony V chloride (0.21 ml, 1.7 mol) were added sequentially to a stirred suspension of methylamine hydrochloride (67.0 g, 1.0 mol) in acetonitrile (500 ml). The mixture was refluxed for 4 hours, during which time chlorine and hydrogen chloride gases were evolved. Further sulfuryl chloride (81.3 ml, 1.0 mol) was added to the mixture, which was then refluxed again for 4 hours. A final portion of sulfuryl chloride (40.7 ml, 0.5 mol) was then added and the mixture was refluxed overnight. The mixture was then cooled to room temperature and the solvent evaporated in vacuo. The residue was distilled (b.p. 55°–57° C./0.02 mBar) to give methylsulfamoyl chloride as a colorless viscous oil (112 g, 86%).

(ii) Methylsulfamoyl chloride (10.0 g, 77 mmol) was added dropwise slowly to a stirred solution of liquid ammonia (ca. 50 ml, excess) in tetrahydrofuran (250 ml) at −40° C. A white precipitate was formed. The mixture was allowed to attain room temperature and the excess ammonia and solvent were evaporated in vacuo. The white crystalline residue was recrystallized from ethyl acetate/hexane to give the title compound as white needles (5.53 g, 65%), m.p. 62°–65° C.

EXAMPLE 3

Preparation of 1-[2-(4,6-dimethoxypyrimidin-2-yl)oxy-3,3-dimethylbutan-1-oyl]-3-methylsulfamide A solution 2-(4,6-dimethoxypyrimidin-2-yl-oxy-3,3-dimethylbutan-1-oic acid (1.35 g, 5.0 mmol) in tetrahydrofuran (20 ml) was added dropwise to a stirred solution of carbonyldiimidazole (0.89 g, 5.5 mmol) in tetrahydrofuran (40 ml) at room temperature. The mixture was heated to reflux for 30 min, then allowed to cool again to room temperature. N-methylsulfamide (0.55 g, 5.0 mmol) was added. After stirring the mixture for 15 min, a solution of 1,8-diazabicyclo[5.4.0]undec-7-ene (0.76 g, 5.0 mmol) in tetrahydrofuran (10 ml) was added to the residue. The mixture was then acidified with 5N hydrochloric acid until there was no further precipitation. The mixture was extracted with ethyl acetate (4×25 ml) and the combined organic phases were dried (sodium sulfate) and evaporated in vacuo. The residue was purified by flash chromatography (dichloromethane/methanol, 97:3) to give the title compound as white crystals (0.97 g, 54%), m.p. 200°–202° C.

EXAMPLES 4 TO 166

By methods analogous to that of Example 3, further compounds of the general formula I were prepared by reaction of compounds of general formula II with compounds of general formula III. Details are given in Tables I and II.

TABLE I

| Ex No | $R^1$ | $R^2$ | $R^3$ | $R^5$ | $R^6$ | mp (°C.) | Yield (%) |
|---|---|---|---|---|---|---|---|
| 4 | $OCH_3$ | $OCH_3$ | $tC_4H_9$ | $CH_3$ | $CH_3$ | 164 | 36 |
| 5 | $OCH_3$ | $OCH_3$ | $tC_4H_9$ | H | $C_6H_5$ | 198 | 69 |
| 6 | $OCH_3$ | $OCH_3$ | $tC_4H_9$ | —$(CH_2)_2O(CH_2)_2$— | | 58 | 39 |
| 7 | $OCH_3$ | $OCH_3$ | $tC_4H_9$ | —$(CH_2)_2N(CH_2)_2$— (N-$CH_3$) | | 225–227 | 19 |
| 8 | $OCH_3$ | $OCH_3$ | $tC_4H_9$ | —$(CH_2)_4$— | | 145–147 | 55 |
| 9 | $OCH_3$ | $OCH_3$ | $tC_4H_9$ | $CH_3$ | $C_6H_5$ | 134–136 | 40 |
| 10 | $OCH_3$ | $OCH_3$ | $tC_4H_9$ | H | $nC_4H_9$ | 164–167 | 49 |
| 11 | $OCH_3$ | $OCH_3$ | $tC_4H_9$ | H | $CH_2C_6H_5$ | 170–171 | 60 |
| 12 | $OCH_3$ | $OCH_3$ | $iC_4H_9$ | $CH_3$ | $CH_3$ | 115–120 | 76 |
| 13 | $CH_3$ | $CH_3$ | $tC_4H_9$ | $CH_3$ | $CH_3$ | 118–120 | 60 |
| 14 | $CH_3$ | $CH_3$ | $iC_4H_9$ | $CH_3$ | $CH_3$ | 133–136 | 74 |
| 15 | $CH_3$ | $CH_3$ | $C_6H_5$ | $CH_3$ | $CH_3$ | 187 | 36 |
| 16 | $OCH_3$ | $OCH_3$ | $C_6H_5$ | H | $C_6H_5$ | 192–193 | 55 |
| 17 | $OCH_3$ | $OCH_3$ | $C_6H_5$ | $CH_3$ | $C_6H_5$ | 137–138 | 55 |
| 18 | $OCH_3$ | Cl | $iC_4H_9$ | $CH_3$ | $CH_3$ | 150–152 | 41 |
| 19 | $OCH_3$ | Cl | $iC_4H_9$ | H | $CH_3$ | 166–168 | 24 |
| 20 | $CH_3$ | $CH_3$ | $nC_4H_9$ | H | $CH_3$ | 154–156 | 42 |
| 21 | $OCH_3$ | $CH_3$ | $tC_4H_9$ | $CH_3$ | $CH_3$ | 123–124 | 56 |
| 22 | $OCH_3$ | $OCH_3$ | $tC_4H_9$ | H | cyclopropyl | 188–189 | 73 |
| 23 | $CH_3$ | $CH_3$ | $sC_4H_9$ | $CH_3$ | $CH_3$ | 150 | 60 |
| 24 | $CH_3$ | $CH_3$ | $sC_4H_9$ | H | $CH_3$ | 161 | 72 |
| 25 | $OCH_3$ | $OCH_3$ | $iC_3H_7$ | $CH_3$ | $CH_3$ | 123–126 | 30 |
| 26 | $OCH_3$ | $OCH_3$ | $iC_3H_7$ | H | $CH_3$ | 166–169 | 73 |
| 27 | $CH_3$ | $CH_3$ | $tC_4H_9$ | H | $CH_3$ | 178–180 | 76 |
| 28 | $CH_3$ | $CH_3$ | $tC_4H_9$ | H | cyclopropyl | 185–186 | 79 |
| 29 | $OCH_3$ | $CH_3$ | $tC_4H_9$ | H | $CH_3$ | 188–189 | 76 |
| 30 | $OCH_3$ | $OCH_3$ | $tC_4H_9$ | H | $CH_2CF_3$ | 159–161 | 54 |
| 31 | $OCH_3$ | $OCH_3$ | $sC_4H_9$ | H | $CH_3$ | 150–153 | 79 |
| 32 | $OCH_3$ | $OCH_3$ | $tC_4H_9$ | H | $nC_3H_7$ | 159–160 | 60 |
| 33 | $OCH_3$ | $OCH_3$ | $tC_4H_9$ | H | $iC_3H_7$ | 172–173 | 58 |
| 34 | $CH_3$ | $CH_3$ | $tC_4H_9$ | H | $nC_4H_9$ | 175–176 | 66 |
| 35 | $OCH_3$ | $OCH_3$ | $nC_4H_9$ | $CH_3$ | $CH_3$ | 122–123 | 53 |
| 36 | $OCH_3$ | $OCH_3$ | $tC_4H_9$ | H | cyclobutyl | 155–158 | 52 |
| 37 | $OCH_3$ | $OCH_3$ | $nC_4H_9$ | H | $CH_3$ | 171–174 | 79 |
| 38 | $OCH_3$ | $OCH_3$ | $tC_4H_9$ | H | thiazolyl | 236–238 | 79 |

TABLE I-continued

| Ex No | R¹ | R² | R³ | R⁵ | R⁶ | mp (°C.) | Yield (%) |
|---|---|---|---|---|---|---|---|
| 39 | OCH₃ | CH₃ | tC₄H₉ | H | 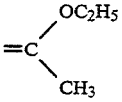 | 190–192 | 59 |
| 40 | CH₃ | CH₃ | nC₄H₉ | CH₃ | CH₃ | 123–124 | 50 |
| 41 | OCH₃ | OCH₃ | sC₄H₉ | CH₃ | CH₃ | 75–77 | 21 |
| 42 | OCH₃ | OCH₃ | tC₄H₉ | H | CH₂CH=CH₂ | 136–139 | 70 |
| 43 | OCH₃ | OCH₃ | tC₄H₉ | H | CH₂C≡CH | 155–156 | 66 |
| 44 | CH₃ | CH₃ | tC₄H₉ | H | —(CH₂)₄— | 115–118 | 42 |
| 45 | OCH₃ | CH₃ | tC₄H₉ | H | CH₃ | 156–159 | 63 |
| 46 | CH₃ | CH₃ | iC₄H₉ | H | CH₃ | 174–176 | 73 |
| 47 | OCH₃ | OCH₃ | iC₄H₉ | H | nC₄H₉ | 133–135 | 59 |
| 48 | CH₃ | CH₃ | tC₄H₉ | —(CH₂)₂O(CH₂)₂— | | 154–156 | 76 |
| 49 | OCH₃ | OCH₃ | tC₄H₉ | H | C₂H₅ | 173–175 | 68 |
| 50 | CH₃ | CH₃ | tC₄H₉ | H | C₂H₅ | 176–178 | 65 |
| 51 | OCH₃ | OCH₃ | iC₃H₇ | H | C₂H₅ | 177–178 | 72 |
| 52 | OCH₃ | OCH₃ | iC₄H₉ | H | C₂H₅ | 147–149 | 74 |
| 53 | CH₃ | CH₃ | iC₄H₉ | H | C₂H₅ | 169–171 | 73 |
| 54 | OCH₃ | OCH₃ | sC₄H₉ | H | C₂H₅ | 142–144 | 77 |
| 55 | CH₃ | CH₃ | nC₄H₉ | H | C₂H₅ | 107–108 | 53 |
| 56 | CH₃ | CH₃ | tC₄H₉ | H | nC₃H₇ | 170–171 | 73 |
| 57 | CH₃ | CH₃ | tC₄H₉ | H | iC₃H₇ | 191–192 | 54 |
| 58 | OCH₃ | OCH₃ | iC₃H₇ | H | nC₃H₇ | 165–167 | 74 |
| 59 | OCH₃ | OCH₃ | iC₃H₇ | H | iC₃H₇ | 179–182 | 57 |
| 60 | CH₃ | CH₃ | nC₃H₇ | H | CH₃ | 151–154 | 58 |
| 61 | OCH₃ | OCH₃ | tC₄H₉ | 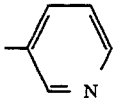 | | 110–113 | 33 |
| 62 | OCH₃ | OCH₃ | tC₄H₉ | H | H | 176 | 63 |
| 63 | OCH₃ | OCH₃ | nC₃H₇ | H | CH₃ | 177–179 | 70 |
| 64 | CH₃ | CH₃ | nC₃H₇ | H | CH₃ | 151–154 | 58 |
| 65 | OCH₃ | OCH₃ | nC₃H₇ | CH₃ | CH₃ | 74–76 | 35 |
| 66 | OCH₃ | OCH₃ | tC₄H₉ | CH₃ | C₂H₅ | 131–134 | 48 |
| 67 | CH₃ | CH₃ | tC₄H₉ | CH₃ | C₂H₅ | 120–122 | 47 |
| 68 | CH₃ | CH₃ | tC₄H₉ | H | CH₂CH=CH₂ | 169–171 | 71 |
| 69 | CH₃ | CH₃ | tC₄H₉ | H | CH₂C≡CH | 155–156 | 51 |
| 70 | OCH₃ | OCH₃ | iC₃H₇ | H | CH₂C≡CH | 165–168 | 80 |
| 71 | OCH₃ | OCH₃ | tC₄H₉ | H | CH₂CO₂CH₃ | 148–151 | 61 |
| 72 | OCH₃ | OCH₃ | sC₄H₉ | H | CH₂C≡CH | 130–134 | 67 |
| 73 | OCH₃ | OCH₃ | tC₄H₉ | CH₃ | OCH₃ | 112–115 | 11 |
| 74 | OCH₃ | OCH₃ | iC₄H₉ | H | CH₂C≡CH | 154–157 | 74 |
| 75 | OCH₃ | OCH₃ | sC₄H₉ | H | CH₂CH=CH₂ | 131–134 | 69 |
| 76 | OCH₃ | OCH₃ | C₆H₅ | H | CH₃ | 191–193 | 69 |
| 77 | OCH₃ | OCH₃ | C₆H₅ | CH₃ | CH₃ | 148–151 | 54 |
| 78 | OCH₃ | OCH₃ | nC₄H₉ | H | CH₂C≡CH | 145–148 | 18 |
| 79 | CH₃ | CH₃ | tC₄H₉ | H | H | 178–181 | 39 |
| 80 | OCH₃ | OCH₃ | sC₄H₉ | H | H | 161–163 | 94 |
| 81 | OCH₃ | OCH₃ | iC₄H₉ | H | H | 157 | 34 |
| 82 | OCH₃ | OCH₃ | nC₃H₇ | H | H | 156–157 | 43 |
| 83 | CH₃ | CH₃ | iC₄H₉ | H | H | 162–163 | 63 |
| 84 | OCH₃ | OCH₃ | sC₄H₉ | CH₃ | C₂H₅ | oil | 76 |
| 85 | OCH₃ | OCH₃ | tC₄H₉ | H | (CH₂)₂Cl | 169–171 | 64 |
| 86 | CH₃ | CH₃ | tC₄H₉ | H | (CH₂)₂Cl | 158–161 | 63 |
| 87 | CH₃ | CH₃ | nC₄H₉ | H | CH₂C≡CH | 106–109 | 32 |
| 88 | OCH₃ | OCH₃ | nC₄H₉ | H | CH₂CH=CH₂ | 152–154 | 15 |
| 89 | CH₃ | CH₃ | iC₄H₉ | H | CH₂CH=CH₂ | 123–126 | 34 |
| 90 | CH₃ | CH₃ | nC₄H₉ | H | CH₂CH=CH₂ | 119–123 | 46 |
| 91 | OCH₃ | OCH₃ | tC₄H₉ | H | CH₂CH(OCH₃)₂ | 149–152 | 72 |
| 92 | CF₃ | OCH₃ | tC₄H₉ | H | H | 93–96 | 24 |
| 93 | CF₃ | OCH₃ | tC₄H₉ | H | CH₃ | 179–181 | 29 |
| 94 | OCH₃ | OCH₃ | tC₄H₉ | H |  | 158–161 | 32 |

TABLE I-continued

| Ex No | R¹ | R² | R³ | R⁵ | R⁶ | mp (°C.) | Yield (%) |
|---|---|---|---|---|---|---|---|
| 95 | OCH₃ | OCH₃ | tC₄H₉ | CH₃ | CH₂C₆H₅ | oil | 29 |
| 96 | OCH₃ | OCH₃ | tC₄H₉ | H | (4,6-dimethylpyrimidin-2-yl) | 156 | 13 |
| 97 | OCH₃ | OCH₃ | nC₃H₇ | H | CH₂CH=CH₂ | 154–156 | 75 |
| 98 | OCH₃ | OCH₃ | nC₃H₇ | H | CH₂C≡CH | 159–161 | 67 |
| 99 | CH₃ | CH₃ | iC₄H₉ | H | CH₂C≡CH | 139–141 | 67 |
| 100 | OCH₃ | OCH₃ | nC₃H₇ | H | cyclopropyl | 183–186 | 43 |
| 101 | OCH₃ | OCH₃ | iC₄H₉ | H | CH₂CH=CH₂ | 138–140 | 45 |
| 102 | OCH₃ | OCH₃ | iC₄H₉ | H | cyclopropyl | 175–177 | 52 |
| 103 | CH₃ | CH₃ | iC₄H₉ | H | cyclopropyl | 160–164 | 58 |
| 104 | OCH₃ | OCH₃ | nC₄H₉ | H | cyclopropyl | 178–182 | 37 |
| 105 | OCH₃ | OCH₃ | sC₄H₉ | H | cyclopropyl | 167–169 | 54 |
| 106 | OCH₃ | OCH₃ | nC₃H₇ | H | C₂H₅ | 160–164 | 56 |
| 107 | OCH₃ | OCH₃ | nC₃H₇ | H | nC₃H₇ | 155–158 | 37 |
| 108 | OCH₃ | OCH₃ | nC₄H₉ | H | C₂H₅ | 170–172 | 21 |
| 109 | OCH₃ | OCH₃ | sC₄H₉ | H | nC₃H₇ | 93–97 | 16 |
| 110 | OCH₃ | OCH₃ | tC₄H₉ | H | OCH₃ | 176–179 | 37 |
| 111 | OCH₃ | OCH₃ | iC₃H₇ | H | H | 166–169 | 93 |
| 112 | OCH₃ | OCH₃ | iC₃H₇ | H | cyclopropyl | 186–188 | 39 |
| 113 | OCH₃ | OCH₃ | iC₃H₇ | H | CH₂CH=CH₂ | 155–157 | 40 |
| 114 | OCH₃ | OCH₃ | OCH₃ | CH₃ | CH₃ | 139–143 | 15 |
| 115 | OCH₃ | OCH₃ | nC₄H₉ | H | H | 169–170 | 52 |
| 116 | OCH₃ | OCH₃ | nC₄H₉ | H | (CH₂)₂Cl | 158–160 | 27 |
| 117 | OCH₃ | OCH₃ | iC₄H₉ | H | (CH₂)₂Cl | 174–175 | 53 |
| 118 | OCH₃ | OCH₃ | sC₄H₉ | H | (CH₂)₂Cl | 147–150 | 43 |
| 119 | OCH₃ | OCH₃ | iC₃H₇ | H | (CH₂)₂Cl | 163–165 | 51 |
| 120 | OCH₃ | OCH₃ | CH₃ | H | nC₄H₉ | 138–141 | 40 |
| 121 | OCH₃ | CH₃ | CH₃ | H | CH₂C₆H₅ | 183–184 | 47 |
| 122 | OCH₃ | OCH₃ | sC₄H₉ | H | nC₄H₉ | 127–129 | 40 |
| 123 | OCH₃ | OCH₃ | sC₄H₉ | H | iC₃H₇ | 156–157 | 11 |
| 124 | OCH₃ | OCH₃ | nC₄H₉ | H | nC₃H₇ | 154–155 | 31 |
| 125 | OCH₃ | OCH₃ | tC₄H₉ | H | (CH₂)₂OCH₃ | 132–135 | 68 |
| 126 | OCH₃ | OCH₃ | CH₃ | H | 2-chlorophenyl | 171–173 | 26 |
| 127 | OCH₃ | OCH₃ | C₆H₅ | H | H | 177–178 | 32 |
| 128 | CH₃ | CH₃ | nC₄H₉ | H | H | 169–170 | 25 |

TABLE I-continued

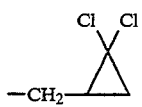

| Ex No | R¹ | R² | R³ | R⁵ | R⁶ | mp (°C.) | Yield (%) |
|---|---|---|---|---|---|---|---|
| 129 | OCH₃ | OCH₃ | tC₄H₉ | H | 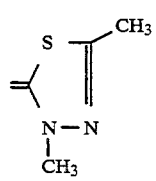 | 156–157 | 53 |
| 130 | OCH₃ | OCH₃ | sC₄H₉ | CH₃ | OCH₃ | 138–144 | 10 |
| 131 | OCH₃ | OCH₃ | C₆H₅ | H | CH₂C₆H₅ | 200–201 | 41 |
| 132 | OCH₃ | OCH₃ | nC₄H₉ | CH₃ | C₂H₅ | 103–104 | 4 |
| 133 | OCH₃ | OCH₃ | sC₄H₉ | H | OCH₃ | 136–137 | 33 |
| 134 | OCH₃ | OCH₃ | C₂H₅ | H | H | 167–168 | 77 |
| 135 | OCH₃ | OCH₃ | C₂H₅ | H | CH₃ | 171–174 | 59 |
| 136 | OCH₃ | OCH₃ | C₂H₅ | CH₃ | CH₃ | oil | 55 |
| 137 | CH₃ | OCH₃ | tC₄H₉ | H | H | 182–184 | 47 |
| 138 | OCH₃ | OCH₃ | tC₄H₉ | C₂H₅ | C₂H₅ | 134–142 | 39 |
| 139 | OCH₃ | OCH₃ | tC₄H₉ | 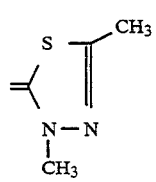 | | 207–211 | 80 |
| 140 | OCH₃ | OCH₃ | sC₄H₉ | 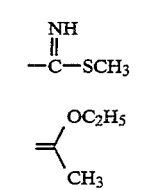 | | 148–151 | 78 |
| 141 | OCH₃ | OCH₃ | tC₄H₉ |  | | 178–180 | 33 |
| 142 | OCH₃ | OCH₃ | iC₃H₇ | 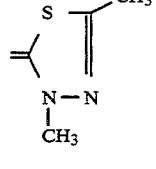 | | 148–150 | 19 |
| 143 | OCH₃ | OCH₃ | iC₃H₇ | 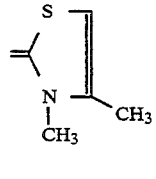 | | 167–170 | 27 |
| 144 | OCH₃ | OCH₃ | tC₄H₉ | 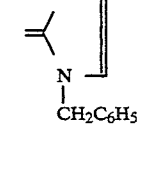 | | 235–238 | 60 |
| 145 | OCH₃ | OCH₃ | iC₄H₉ |  | | 187–189 | 63 |

TABLE I-continued
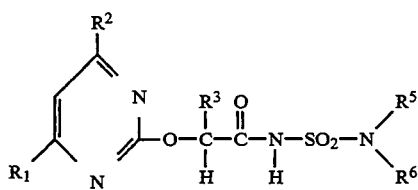
| Ex No | R¹ | R² | R³ | R⁵ | R⁶ | mp (°C.) | Yield (%) |
|---|---|---|---|---|---|---|---|
| 146 | OCH₃ | OCH₃ | iC₄H₉ | | (S-C(CH₃)=N-N(CH₃)-N=C(CH₃)) | 178–179 | 11 |
| 147 | OCH₃ | OCH₃ | nC₄H₉ | | (S-C(CH₃)=N-N(CH₃)-N=C(CH₃)) | 160–162 | 13 |
| 148 | OCH₃ | OCH₃ | nC₃H₇ | | (S-C(CH₃)=N-N(CH₃)-N=C(CH₃)) | 171–173 | 12 |
| 149 | OCH₃ | OCH₃ | tC₄H₉ | | =C(H)N(CH₃)₂ | 187–191 | 54 |
| 150 | OCH₃ | OCH₃ | sC₄H₉ | | (S-C=N(CH₃)-CH=CH) | 172–176 | 58 |
| 151 | OCH₃ | OCH₃ | iC₄H₉ | | (S-C=N(CH₃)-CH=CH) | 183–185 | 11 |
| 152 | CH₃ | CH₃ | tC₄H₉ | | (S-C=N(CH₃)-CH=CH) | 175–176 | 35 |
| 153 | CH₃ | OCH₃ | tC₄H₉ | | (S-C=N(CH₃)-CH=CH) | 181–184 | 55 |
| 154 | OCH₃ | OCH₃ | sC₄H₉ | | =C(OC₂H₅)CH₃ | 111–112 | 38 |

TABLE I-continued

Structure:
R² attached via C=N to ring with R¹, N; ring-O-C(R³)(H)-C(=O)-N(H)-SO₂-N(R⁵)(R⁶)

| Ex No | R¹ | R² | R³ | R⁵ R⁶ | mp (°C.) | Yield (%) |
|---|---|---|---|---|---|---|
| 155 | OCH₃ | OCH₃ | iC₄H₉ | OC₂H₅ / CH₃ (cyclic) | 126–128 | 39 |
| 156 | OCH₃ | OCH₃ | nC₄H₉ | OC₂H₅ / CH₃ (cyclic) | 129–130 | 41 |
| 157 | CH₃ | CH₃ | tC₄H₉ | OC₂H₅ / CH₃ (cyclic) | 151–153 | 22 |
| 158 | CH₃ | OCH₃ | tC₄H₉ | OC₂H₅ / CH₃ (cyclic) | oil | 28 |

TABLE II

Structure as above.

| Ex No | R¹ | R² | R³ | R⁵ | R⁶ | mp (°C.) | Yield (%) |
|---|---|---|---|---|---|---|---|
| 159 | OCH₃ | OCH₃ | tC₄H₉ | H | H | 145–148 | 62 |
| 160 | OCH₃ | OCH₃ | tC₄H₉ | H | CH₃ | 187–188 | 54 |
| 161 | OCH₃ | OCH₃ | tC₄H₉ | CH₃ | CH₃ | oil | 32 |
| 162 | OCH₃ | OCH₃ | tC₄H₉ | CH₃ | C₂H₅ | oil | 21 |
| 163 | CH₃ | OCH₃ | tC₄H₉ | H | CH₃ | 141–144 | 35 |
| 164 | CH₃ | OCH₃ | tC₄H₉ | H | H | 179–180 | 65 |
| 165 | OCH₃ | OCH₃ | tC₄H₉ | \multicolumn{2}{|}{OC₂H₅ / CH₃ (cyclic)} | oil | 16 |
| 166 | OCH₃ | OCH₃ | tC₄H₉ | \multicolumn{2}{|}{S / N-CH₃ (thiazoline ring)} | 200–104 | 39 |

Elemental analysis or n.m.r. data for the compounds of general formula I described above is set out in Table III below.

TABLE II

¹H n.m.r. - chemical shift, δ, in p.p.m.
for solutions in CDCl₃ (unless otherwise indicated)
or Analysis %

| Ex No | C Calc. | C Found | H Calc. | H Found | N Calc. | N Found |
|---|---|---|---|---|---|---|
| 3 | 43.1 | 43.3 | 6.1 | 6.2 | 15.5 | 15.5 |
| 4 | 44.7 | 44.9 | 6.4 | 6.7 | 14.9 | 15.0 |
| 5 | 50.9 | 51.2 | 5.7 | 6.0 | 13.2 | 13.1 |

TABLE II-continued

¹H n.m.r. - chemical shift, δ, in p.p.m.
for solutions in CDCl₃ (unless otherwise indicated)
or Analysis %

| Ex No | C Calc. | C Found | H Calc. | H Found | N Calc. | N Found |
|---|---|---|---|---|---|---|
| 6 | \multicolumn{6}{|}{1.1(9H, s), 3.3(4H, m), 3.7(4H, m), 3.9(6H, s), 4.9(1H, s), 5.7(1H, s), 8.4(1H, br.s)} |
| 7 | 47.3 | 47.4 | 6.8 | 6.9 | 16.2 | 16.0 |
| 8 | \multicolumn{6}{|}{1.1(9H, s), 1.9(4H, m), 3.3–3.5(4H, m), 3.9(6H, s), 4.9(1H, s), 5.8(1H, s), 8.5(1H, br.s)} |
| 9 | 52.0 | 52.1 | 6.0 | 6.2 | 12.8 | 12.8 |
| 10 | \multicolumn{6}{|}{0.9(3H, t), 1.1(9H, s), 1.3(2H, m), 1.5(2H, m),} |

TABLE II-continued $^1$H n.m.r. - chemical shift, δ, in p.p.m. for solutions in CDCl$_3$ (unless otherwise indicated) or Analysis %

| Ex No | C Calc. | C Found | H Calc. | H Found | N Calc. | N Found |
|---|---|---|---|---|---|---|
| | 2.9(2H, q), 3.9(6H, s), 4.9(1H, s), 5.1(1H, br.t), 5.8(1H, s), 8.5(1H, br.s) | | | | | |
| 11 | 52.0 | 52.1 | 6.0 | 6.3 | 12.8 | 12.8 |
| 12 | 44.7 | 44.4 | 6.4 | 6.6 | 14.9 | 14.6 |
| 13 | 48.8 | 49.0 | 7.0 | 6.8 | 16.3 | 16.2 |
| 14 | 48.8 | 48.9 | 7.0 | 7.0 | 16.3 | 16.1 |
| 15 | 52.7 | 53.1 | 5.5 | 5.6 | 15.4 | 15.5 |
| 16 | 54.0 | 54.3 | 4.5 | 4.5 | 12.6 | 12.6 |
| 17 | 55.0 | 55.1 | 4.8 | 4.8 | 12.2 | 12.2 |
| 18 | 41.0 | 41.1 | 5.6 | 5.6 | 14.7 | 14.6 |
| 19 | 39.3 | 40.1 | 5.2 | 5.3 | 15.3 | 15.2 |
| 20 | 47.3 | 47.7 | 6.7 | 6.8 | 17.0 | 17.1 |
| 21 | 46.7 | 46.9 | 6.7 | 6.8 | 15.5 | 15.4 |
| 22 | 46.4 | 46.4 | 6.2 | 6.2 | 14.4 | 14.4 |
| 23 | 48.8 | 48.5 | 7.0 | 6.9 | 16.3 | 16.1 |
| 24 | 47.3 | 47.3 | 6.7 | 6.6 | 17.0 | 16.8 |
| 25 | 43.1 | 43.4 | 6.1 | 5.7 | 15.5 | 15.5 |
| 26 | 41.4 | 41.3 | 5.8 | 5.9 | 16.1 | 16.1 |
| 27 | 47.3 | 47.2 | 6.7 | 6.7 | 17.0 | 16.9 |
| 28 | 50.5 | 50.7 | 6.8 | 6.7 | 15.7 | 15.8 |
| 29 | 45.1 | 45.2 | 6.4 | 6.3 | 16.2 | 16.3 |
| 30 | 39.1 | 39.2 | 4.9 | 5.0 | 13.0 | 12.9 |
| 31 | 43.1 | 43.5 | 6.1 | 6.0 | 15.5 | 15.7 |
| 32 | 46.1 | 46.1 | 6.7 | 6.7 | 14.3 | 14.5 |
| 33 | 46.1 | 45.9 | 6.7 | 6.7 | 14.3 | 14.1 |
| 34 | 51.6 | 51.6 | 7.6 | 7.3 | 15.0 | 15.1 |
| 34 | 44.7 | 44.8 | 6.4 | 6.4 | 14.9 | 15.0 |
| 36 | 1.1(9H, s), 1.5-2.3(6H, m), 3.7(1H, m), 3.9(6H, s), 5.0(1H, s), 5.4(1H, d), 5.7(1H, s), 8.5(1H, br.s) | | | | | |
| 37 | 43.1 | 43.1 | 6.1 | 6.1 | 15.5 | 15.2 |
| 38 | 43.1 | 43.4 | 5.2 | 5.2 | 15.7 | 15.8 |
| 39 | 48.4 | 48.2 | 6.5 | 6.4 | 15.0 | 14.9 |
| 40 | 48.8 | 49.1 | 7.0 | 7.0 | 16.3 | 16.4 |
| 41 | 0.8(3H, t), 1.0(3H, m), 1.2(1H, m), 1.5(1H, m), 2.0(1H, m), 2.8(2x3H, s), 3.8(6H, s), 5.1 and 5.3(1H, 2xd), 5.7(1H, s), 8.5(1H, br.s) | | | | | |
| 42 | 46.4 | 46.2 | 6.2 | 6.6 | 14.4 | 14.5 |
| 43 | 46.6 | 46.0 | 5.7 | 5.9 | 14.5 | 14.4 |
| 44 | 1.1(9H, s), 1.8(4H, m), 2.4(6H, s), 3.4(4H, m), 5.0(1H, s), 6.7(1H, s), 8.4(1H, br.s) | | | | | |
| 45 | 43.1 | 42.8 | 6.1 | 6.1 | 15.5 | 15.8 |
| 46 | 47.3 | 46.8 | 6.7 | 6.7 | 17.0 | 17.1 |
| 47 | 47.5 | 47.4 | 7.0 | 7.0 | 13.9 | 14.2 |
| 48 | 49.7 | 49.8 | 6.8 | 6.9 | 14.5 | 14.7 |
| 49 | 44.7 | 44.5 | 6.4 | 6.5 | 14.9 | 15.1 |
| 50 | 48.8 | 48.5 | 7.0 | 7.1 | 16.3 | 16.3 |
| 51 | 43.1 | 42.6 | 6.1 | 6.2 | 15.5 | 15.6 |
| 52 | 0.9(6H, dd), 1.1(3H, t), 1.7(1H, m), 1.8(2H, m), 2.9(2H, q), 3.8(6H, s), 5.2(1H, br.t), 5.3(1H, dd), 5.7(1H, s), 8.6(1H, br.s) | | | | | |
| 53 | 0.9(6H, dd), 1.1(3H, t), 1.7-1.9(2H, m), 2.4(6H, s), 3.0(2H, m), 5.1(1H, br.t), 5.5(1H, dd), 6.7(1H, s), 8.9(1H, br.s) | | | | | |
| 54 | 1.0(3H, m), 1.1(3H, dd), 1.2(3H, dt), 1.2-1.6(2H, m), 2.0(1H, m), 3.0(2H, m), 3.9(6H, s), 5.1(1H, br.m), 5.2 and 5.4(1H, 2xd), 5.8(1H, s), 8.6(1H, br.s) | | | | | |
| 55 | 48.8 | 48.4 | 7.0 | 7.0 | 16.3 | 16.4 |
| 56 | 0.9(3H, t), 1.1(9H, s), 1.5(2H, m), 2.5(6H, s), 2.8(2H, q), 5.1(1H, s), 5.2(1H, br.t), 6.7(1H, s), 8.5(1H, br.s) | | | | | |
| 57 | 1.0(6H, dd), 1.1(9H, s), 2.4(6H, s), 3.4(1H, m), 5.0(1H, br.d), 5.1(1H, s), 6.7(1H, s), 8.5(1H, br.s) | | | | | |
| 58 | 0.9(3H, t), 1.1(6H, dd), 1.5(2H, m), 2.3(1H, m), 2.9(2H, m), 3.9(6H, s), 5.1(1H, s), 5.2(1H, s), 5.7(1H, s), 8.5(1H, br.s) | | | | | |
| 59 | 1.1(6H, dd), 1.2(6H, dd), 2.8(1H, m), 3.5(1H, m), 3.9(6H, s), 5.0(1H, br.d), 5.2(1H, d), 5.7(1H, s), 8.6(1H, br.s) | | | | | |
| 60 | 0.9(3H, t), 1.5(2H, m), 2.0(2H, m), 2.4(6H, s), 2.7(3H, d), 5.3(1H, br.q), 5.4(1H, t), 6.7(1H, s), 9.0(1H, br.s) | | | | | |
| 61 | 1.1(9H, s), 1.2(3H, t), 2.5(3H, s), 3.9(6H, s), 4.1(2H, q), 4.8(1H, s), 5.7(1H, s), 8.8(1H, br.s) | | | | | |
| 62 | 1.1(9H, s), 3.9(6H, s), 5.0(1H, s), 5.6(2H, br.s), 5.7(1H, s), 9.0(1H, br.s) | | | | | |
| 63 | 1.0(3H, t), 1.5(2H, m), 2.0(2H, m), 2.7(3H, d), 3.9(6H, s), 5.2(1H, br.q), 5.3(1H, t), 5.7(1H, s), 8.7(1H, br.s) | | | | | |
| 64 | 0.9(3H, t), 1.5(2H, m), 2.0(2H, m), 2.4(6H, s), 2.6(3H, d), 5.4(1H, q), 5.5(1H, t), 6.8(1H, S), 9.0(1H, br s) | | | | | |
| 65 | 43.1 | 42.5 | 6.1 | 6.4 | 15.5 | 15.5 |
| 66 | 46.1 | 46.3 | 6.7 | 6.8 | 14.3 | 14.7 |
| 67 | 50.3 | 50.2 | 7.3 | 7.3 | 15.6 | 15.7 |
| 68 | 1.1(9H, s), 1.7(1H, br s), 2.4(6H, s), 3.5(2H, m), 5.2-5.0(3H, m), 5.7(1H, m), 6.8(1H, s), 8.6(1H, br s) | | | | | |
| 69 | 1.1(9H, s), 1.7(1H, br s), 2.2(1H, t), 2.4(6H, s), 3.8(2H, m), 5.5(1H, br s), 6.7(1H, s), 8.7(1H, br s) | | | | | |
| 70 | 1.0(3H, d), 1.1(3H, d), 2.2(1H, t), 2.3(1H, m), 3.8(2H, d), 3.9(6H, s), 5.2(1H, d), 5.7(1H, s) | | | | | |
| 71 | 1.1(9H, s), 3.7(3H, s), 3.8(2H, s), 3.9(6H, s), 4.9(1H, s), 5.7(1H, s) | | | | | |
| 72 | 46.6 | 47.1 | 5.7 | 5.8 | 14.5 | 14.5 |
| 73 | 1.1(9H, s), 1.6(1H, br s), 3.0(3H, s), 3.6(3H, s), 3.9(9H, s), 4.9(1H, s), 5.7(1H, s) | | | | | |
| 74 | 46.6 | 47.0 | 5.7 | 6.1 | 14.5 | 14.7 |
| 75 | 46.4 | 46.6 | 6.2 | 6.5 | 14.4 | 14.6 |
| 76 | 47.1 | 47.3 | 4.7 | 5.0 | 14.7 | 14.9 |
| 77 | 48.5 | 48.8 | 5.1 | 5.3 | 14.1 | 14.2 |
| 78 | 0.9(3H, t), 1.3-1.6(4H, m), 1.9-2.1(2H, q), 2.2(1H, t), 3.8(2H, br d), 3.9(6H, s), 5.3(1H, dd), 5.8(1H, s) | | | | | |
| 79 | 45.6 | 45.4 | 6.4 | 6.6 | 17.7 | 17.7 |
| 80 | 41.4 | 40.6 | 5.8 | 6.1 | 16.1 | 15.7 |
| 81 | 41.4 | 41.8 | 5.8 | 6.2 | 16.1 | 16.4 |
| 82 | 39.5 | 39.4 | 5.4 | 5.6 | 16.8 | 16.8 |
| 83 | 45.6 | 45.8 | 6.4 | 6.7 | 17.7 | 17.5 |
| 84 | 0.9(3H, q), 1.0-1.8(8H, m), 2.1(1H, m), 2.9(3H, 2xs), 3.3(2H, m), 3.6(1H, m), 3.8(6H, s), 5.1 and 5.2(1H, 2 x d), 5.7(1H, s), 8.5(1H, br s) | | | | | |
| 85 | 40.9 | 41.2 | 5.6 | 6.0 | 13.6 | 13.7 |
| 86 | 44.4 | 44.0 | 6.1 | 6.4 | 14.8 | 14.8 |
| 87 | 0.9(3H, t), 1.2-1.5(4H, m), 2.0(2H, br q), 2.2(1H, t), 2.4(6H, s), 3.8(2H, br m), 5.4(1H, dd), 5.6(1H, br s), 6.7(1H, s) | | | | | |
| 88 | 46.4 | 46.3 | 6.2 | 6.4 | 14.4 | 14.5 |
| 89 | 1.0(6H, dd), 1.6-2.0(3H, m), 2.4(6H, s), 3.5(2H, br s), 5.1-5.4(4H, m), 5.7(1H, m), 6.8(1H, s) | | | | | |
| 90 | 50.6 | 49.9 | 6.8 | 7.0 | 15.7 | 15.8 |
| 91 | 44.0 | 44.1 | 6.5 | 6.8 | 12.8 | 12.9 |
| 92 | 37.3 | 38.0 | 4.4 | 4.8 | 14.5 | 14.6 |
| 93 | 39.0 | 39.2 | 4.8 | 5.0 | 14.0 | 13.9 |
| 94 | 48.0 | 47.5 | 5.4 | 5.6 | 16.5 | 17.2 |
| 95 | 1.0(9H, s), 2.6(3H, s), 3.8(6H, s), 4.3(2H, s), 4.8(1H, s), 5.7(1H, s), 8.7(1H, br s) | | | | | |
| 96 | 1.0(9H, s), 2.3(6H, s), 2.4(6H, s), 3.8(6H, s), 4.7(1H, s), 5.5(1H, s), 6.4(1H, s) | | | | | |
| 97 | 1.0(3H, m), 1.5(2H, m), 2.0(2H, m), 3.6(2H, br m), 3.9(6H, s), 5.1-5.3(3H, m), 5.7(1H, m) | | | | | |
| 98 | 44.2 | 44.9 | 5.4 | 5.3 | 15.1 | 14.6 |
| 99 | 1.0(6H, dd), 1.8-2.0(3H, m), 2.2(1H, t), 2.4(6H, s), 3.8(2H, m), 5.5(1H, dd), 5.6(1H, br s), 6.7(1H, s) | | | | | |
| 100 | 44.9 | 44.6 | 5.9 | 6.1 | 15.0 | 14.7 |
| 101 | 46.4 | 46.2 | 6.2 | 6.5 | 14.4 | 14.3 |
| 102 | 46.4 | 46.1 | 6.2 | 6.3 | 14.4 | 14.5 |
| 103 | 0.6(2H, m), 0.7(2H, m), 0.9(6H, dd), 1.7-2.0(2H, m), 2.2(1H, m), 2.4(6H, s), 5.5(1H, dd), 5.7(1H, br s) | | | | | |
| 104 | 0.7(2H, m), 0.8(2H, m), 0.9(3H, t), 1.3-1.6(4H, m), 2.0(2H, q), 2.1(1H, br s), 2.3(1H, m), 3.9(6H, s), 5.3(1H, t), 5.7(1H, s), 9.1(1H, br s) | | | | | |
| 105 | 46.4 | 46.8 | 6.2 | 6.4 | 14.4 | 14.8 |
| 106 | 43.1 | 43.4 | 6.1 | 6.4 | 15.5 | 15.9 |
| 107 | 44.7 | 44.8 | 6.4 | 6.7 | 14.9 | 15.0 |
| 108 | 44.7 | 45.0 | 6.3 | 6.6 | 14.9 | 14.9 |
| 109 | 0.8-0.9(6H, 2xm), 1.0(3H, 2xd), 1.3-1.7(4H, m), 2.0(1H, m), 2.9(2H, q), 3.9(6H, s), 5.6(1H, m), 5.7(1H, 2xd) | | | | | |
| 110 | 1.0(9H, s), 1.8(1H, br s), 3.7(3H, s), 3.8(6H, s), 4.9(1H, s), 5.7(1H, s), 8.0(1H, br s) | | | | | |
| 111 | 44.3 | 44.8 | 2.9 | 3.1 | 21.5 | 21.9 |
| 112 | 44.9 | 44.3 | 5.9 | 5.9 | 14.7 | 15.0 |
| 113 | 44.9 | 44.2 | 5.9 | 5.6 | 14.7 | 14.8 |
| 114 | 1.6(3H, d), 2.9(6H, s), 3.9(6H, s), 5.3(1H, q), 5.7(1H, s), 8.5(1H, br s) | | | | | |

TABLE II-continued

¹H n.m.r. - chemical shift, δ, in p.p.m.
for solutions in CDCl₃ (unless otherwise indicated)
or Analysis %

| Ex No | C Calc. | C Found | H Calc. | H Found | N Calc. | N Found |
|---|---|---|---|---|---|---|
| 115 | 41.4 | 41.2 | 5.8 | 5.8 | 16.1 | 15.8 |
| 116 | 40.9 | 41.1 | 5.6 | 5.8 | 13.6 | 13.6 |
| 117 | 40.9 | 40.7 | 5.6 | 5.6 | 13.6 | 13.7 |
| 118 | 40.9 | 40.7 | 5.6 | 5.7 | 13.6 | 13.7 |
| 119 | 39.4 | 40.0 | 5.3 | 5.9 | 14.1 | 14.6 |
| 120 | 43.0 | 42.6 | 6.1 | 6.8 | 15.5 | 16.1 |
| 121 | 48.5 | 48.7 | 5.1 | 5.6 | 14.1 | 14.8 |
| 122 | 47.5 | 48.0 | 7.0 | 7.6 | 13.9 | 14.7 |
| 123 | 46.1 | 45.5 | 6.1 | 6.8 | 14.4 | 14.8 |
| 124 | 46.1 | 45.8 | 6.7 | 6.7 | 14.4 | 15.0 |
| 125 | 1.1(9H, s), 3.1(2H, br m), 3.3(3H, s), 3.4(2H, t), 3.9(6H, s), 4.9(1H, s), 5.6(1H, br s), 5.7(1H, s) ||||||
| 126 | 43.2 | 43.2 | 4.1 | 4.5 | 13.4 | 13.8 |
| 127 | 45.7 | 45.2 | 4.4 | 4.8 | 15.2 | 15.3 |
| 128 | 45.6 | 44.9 | 6.4 | 6.6 | 17.7 | 17.8 |
| 129 | 1.0(9H, s), 1.2(1H, d t), 1.6(1H, d d), 1.9(1H m), 3.0(1H, m), 3.3(1H, m), 3.9(6H, s), 4.9(1H, s), 5.6(1H, br m), 5.7(1H, s), 8.6(1H, br s) ||||||
| 130 | 0.8–1.0(6H, m), 1.2–1.7(2H, m), 2.0(1H, m), 2.6(3H, s), 3.6(3H, s), 3.9(6H, s), 4.9(1H, 2xd), 5.7(1H, s) (in d⁶-DMSO) ||||||
| 131 | 1.8(1H, br s), 3.9(6H, s), 4.0(1H, m), 4.1(1H dd), 5.5(1H, br t), 5.7(1H, s), 6.1(1H, s), 7.0–7.5(10H, m), 9.2(1H, br s) ||||||
| 132 | 46.1 | 45.8 | 6.7 | 6.9 | 14.4 | 14.4 |
| 133 | 41.3 | 41.4 | 5.9 | 5.7 | 14.8 | 14.9 |
| 134 | 37.5 | 37.2 | 5.0 | 5.6 | 17.5 | 17.4 |
| 135 | 39.5 | 39.1 | 5.4 | 5.8 | 16.8 | 16.7 |
| 136 | 1.0(3H, t), 2.0(2H, m), 2.8(6H, s), 3.3(6H, s), 5.0(1H, t), 5.6(1H, s), 8.9(1H, br s) ||||||
| 137 | 43.1 | 42.5 | 6.1 | 6.4 | 15.5 | 15.5 |
| 138 | 47.5 | 46.9 | 7.0 | 7.6 | 13.9 | 13.9 |
| 139 | 41.7 | 42.3 | 5.3 | 5.7 | 18.2 | 17.7 |
| 140 | 41.7 | 41.8 | 5.3 | 5.3 | 18.2 | 18.2 |
| 141 | 1.1(9H, s), 1.7(1H, br s), 2.3(3H, s), 3.9(H, s), 4.3(1H, s), 5.7(1H, s), 8.5(1H, br s) ||||||
| 142 | 44.6 | 45.2 | 6.0 | 6.4 | 13.9 | 14.1 |
| 143 | 40.4 | 40.8 | 5.0 | 5.2 | 18.8 | 19.1 |
| 144 | 44.8 | 44.3 | 5.5 | 5.7 | 15.2 | 15.2 |
| 145 | 50.7 | 49.9 | 5.2 | 5.0 | 13.4 | 13.4 |
| 146 | 41.8 | 41.1 | 5.3 | 5.0 | 18.3 | 18.0 |
| 147 | 41.7 | 41.1 | 5.3 | 5.3 | 18.3 | 18.2 |
| 148 | 40.4 | 40.7 | 5.0 | 5.2 | 18.8 | 18.4 |
| 149 | 1.0(9H, s), 2.8(3H, s), 3.1(3H, s), 3.9(6H, s), 3.6(1H, s), 5.8(1H, s), 8.0(1H, s), 11.6(1H, s) ||||||
| 150 | 50.3 | 50.2 | 7.3 | 7.3 | 15.6 | 15.7 |
| 151 | 47.5 | 47.1 | 7.0 | 7.2 | 13.9 | 13.4 |
| 152 | 46.5 | 45.6 | 5.6 | 6.1 | 16.9 | 16.7 |
| 153 | 44.7 | 44.1 | 5.4 | 5.8 | 16.3 | 16.2 |
| 154 | 45.9 | 45.4 | 6.3 | 6.8 | 13.4 | 13.6 |
| 155 | 45.9 | 45.4 | 6.3 | 6.8 | 13.4 | 13.4 |
| 156 | 45.9 | 45.5 | 6.3 | 6.7 | 13.4 | 13.4 |
| 157 | 1.1(9H, s), 1.3(6H, t), 2.4(6H, s), 2.5(3H, s), 4.1(2H, q), 5.1(1H, 2xs), 6.7(1H, s), 8.7(1H, br s) ||||||
| 158 | 1.0(9H, s), 1.2(3H, t), 2.2(3H, s), 2.4(3H, s), 3.7(3H, s), 4.0(2H, q), 4.8(1H, s), 6.1(1H, s), 8.9(1H, br s) ||||||
| 159 | 1.0(9H, s), 3.9(6H, s), 4.8(1H, s), 7.5(2H, s), 11.8(1H, s), (in d⁶-DMSO) ||||||
| 160 | 1.0(9H, s), 2.5(3H, br d), 3.9(6H, s), 4.8(1H, s) 7.5(1H, br q), 11.8(1H, br s), (in d⁶-DMSO) ||||||
| 161 | 1.0(9H, 2), 2.8(6H, s), 4.0(9H, s), 5.0(1H, s), 8.4(1H, br s) ||||||
| 162 | 1.0(9H, s), 1.1(3H, t), 2.8(3H, s), 3.3(2H, q), 3.9(6H, s), 4.9(1H, s), 8.7(1H, br s) ||||||
| 163 | 1.1(9H, s), 2.5(3H, s), 2.7(3H, d), 4.0(3H, s), 5.0(1H, s), 5.2(1H, br q) ||||||
| 164 | 1.1(9H, s), 2.4(3H, s), 4.0(3H, s), 4.7(1H, s), 7.5(2H, br s), 11.8(1H, br s) (in d⁶-DMSO) ||||||
| 165 | 1.0(9H, s), 1.2(3H, t), 2.4(3H, s), 3.9(6H, s), 4.0(2H, m), 4.8(1H, s), 9.5(1H, br s) ||||||
| 166 | 40.4 | 40.4 | 5.0 | 5.5 | 18.8 | 18.1 |

EXAMPLE 167

Herbicidal Activity

To evaluate their herbicidal activity, compounds according to the invention were tested using as representative range of plants: maize, Zea Mays (Mz); rice, Oryza sativa (R); barnyard grass, Echinochloa crusgalli (BG); oat, Avena sativa (O); linseed, Linum usitatissimum (L); mustard, Sinapsis alba (M); sugar beet, Beta vulgaris (SB); and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of tests, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trademark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table IV below, in which the compounds are identified by reference to the preceding Examples. Absence of a numeral in the Table indicates a zero rating; an asterisk indicates that no result was obtained.

TABLE IV

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 3 | 7 | 7 | 7 | 6 | 7 | 8 | 7 | 8 | 5 | 7 | 7 | 8 | 7 | 7 | 9 | 9 | 7 | 8 | 8 | 8 | 7 | 8 | 8 | 8 | 8 |
| | | | | | | | | | 1 | 2 | 6 | 7 | 4 | 7 | 9 | 9 | 8 | 6 | 7 | 6 | 6 | 2 | 7 | 8 | 8 | 3 |

TABLE IV-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 4 | 5 | 8 | 9 | 8 | 8 | 9 | 9 | 7 | 5 | 8 | 8 | 8 | 8 | 8 | 9 | 8 | 8 | 8 | 9 | 9 | 8 | 9 | 8 | 8 | 6 |
| | | | | | | | | | 1 | 5 | 5 | 8 | 7 | 8 | 8 | 8 | 8 | 3 | 6 | 8 | 4 | 8 | 8 | 8 | 4 |
| 5 | 4 | 6 | 6 | 5 | 5 | 6 | 7 | 5 | 5 | | 5 | 8 | 4 | 5 | 8 | 8 | 7 | 7 | 7 | 5 | | 2 | 7 | 7 | 6 |
| | | | | | | | | | 1 | | 2 | 2 | 1 | | 7 | 7 | 4 | 5 | 2 | | | | 5 | 5 | 4 |
| 6 | 6 | 6 | 6 | 4 | 7 | 8 | 8 | 6 | 5 | 6 | 7 | 9 | 7 | 8 | 8 | 9 | 8 | 8 | 8 | 6 | 6 | 7 | 8 | 7 | 4 |
| | | | | | | | | | 1 | 2 | 5 | 8 | 3 | 7 | 8 | 8 | 7 | 2 | 2 | 1 | | 2 | 7 | 5 | 1 |
| 7 | | | | | | | | | 5 | | | 4 | 2 | 2 | 8 | 7 | 5 | | | | | | | | |
| | | | | | | | | | 1 | | | | | | 7 | 5 | | | | | | | | | |
| 8 | 7 | 7 | 6 | 5 | 6 | 9 | 8 | 7 | 5 | 8 | 8 | 8 | 8 | 7 | 9 | 9 | 8 | 7 | 8 | 6 | 7 | 7 | 7 | 8 | 8 |
| | | | | | | | | | 1 | 2 | 3 | 7 | 3 | 7 | 8 | 8 | 8 | 3 | 6 | 2 | | 3 | 7 | 7 | 3 |
| 9 | 4 | 6 | 6 | 4 | 5 | 7 | 7 | 4 | 5 | 3 | 3 | 7 | 3 | 5 | 9 | 8 | 4 | 6 | 7 | 7 | 6 | 7 | 8 | 8 | 4 |
| | | | | | | | | | 1 | | | 3 | | 8 | 8 | 8 | 2 | 2 | 5 | | 2 | | 7 | 8 | 3 |
| 10 | 8 | 7 | 7 | 8 | 8 | 9 | 7 | 7 | 5 | 6 | 7 | 7 | 7 | 8 | 8 | 8 | 7 | 8 | 8 | 8 | 8 | 8 | 8 | 8 | 7 |
| | | | | | | | | | 1 | 4 | 5 | 6 | 6 | 7 | 7 | 7 | 6 | 5 | 7 | 6 | 5 | 3 | 8 | 7 | |
| 11 | 2 | 4 | 3 | | 5 | 7 | 7 | 5 | 5 | 7 | 7 | 8 | 7 | 8 | 9 | 9 | 8 | 8 | 8 | 9 | 7 | 8 | 8 | 8 | 8 |
| | | | | | | | | | 1 | 2 | 6 | 8 | 5 | 8 | 8 | 8 | 7 | | 6 | 5 | 3 | 4 | 7 | 5 | |
| 12 | 4 | 6 | 6 | 4 | 5 | 8 | 8 | 5 | 5 | 7 | 8 | 8 | 5 | 8 | 9 | 9 | 8 | 8 | 8 | 8 | 6 | 8 | 8 | 8 | 8 |
| | | | | | | | | | 1 | | 6 | 8 | 2 | 7 | 8 | 8 | 7 | 2 | 4 | 5 | 3 | 6 | 8 | 8 | 2 |
| 13 | 8 | 6 | 8 | 7 | 8 | 9 | 9 | * | 5 | 9 | 8 | 9 | 7 | 8 | 9 | 9 | 8 | 9 | 9 | 9 | 8 | 8 | 8 | 8 | 8 |
| | | | | | | | | | 1 | 7 | 7 | 9 | 5 | 8 | 9 | 9 | 7 | 6 | 6 | 7 | 4 | 7 | 8 | 8 | 6 |
| 14 | 8 | 7 | 8 | 7 | 6 | 9 | 9 | 7 | 5 | 7 | 7 | 8 | 7 | 7 | 9 | 9 | 8 | 8 | 9 | 9 | 7 | 7 | 8 | 9 | 7 |
| | | | | | | | | | 1 | 4 | 6 | 7 | 6 | 3 | 8 | 8 | 6 | 5 | 7 | 6 | 5 | 5 | 8 | 8 | |
| 15 | 6 | 6 | 7 | 6 | 4 | 9 | 9 | | 5 | 5 | 5 | 7 | 6 | 7 | 9 | 9 | 2 | 6 | 8 | 6 | 6 | 1 | 7 | 8 | |
| | | | | | | | | | 1 | 1 | 4 | 6 | 2 | 2 | 8 | 8 | | 2 | 5 | | 2 | | 7 | 7 | |
| 16 | | | 4 | | 4 | 6 | 3 | 2 | 5 | | | | | 8 | 6 | 7 | | 3 | 2 | 2 | 2 | 4 | 7 | 7 | 4 |
| | | | | | | | | | 1 | | | | | 7 | 6 | 2 | | | | 2 | 2 | 2 | 6 | 6 | |
| 17 | 3 | 2 | 5 | 2 | 5 | 6 | | 2 | 5 | 3 | | 2 | | 5 | 9 | 8 | 7 | 2 | | 2 | | | 6 | 7 | 4 |
| | | | | | | | | | 1 | | | | | | 7 | 6 | 2 | | | | | | 6 | 6 | |
| 18 | 6 | 3 | 2 | 1 | 4 | 7 | 4 | 3 | 5 | 4 | 4 | 7 | 3 | 6 | 9 | 8 | 6 | 5 | 7 | 7 | 3 | 6 | 7 | 8 | 6 |
| | | | | | | | | | 1 | 4 | | 6 | 2 | 4 | 8 | 6 | 5 | | | | | | 7 | 7 | 2 |
| 19 | 6 | 7 | * | 3 | 2 | 7 | 7 | 1 | 5 | 6 | 6 | 7 | 2 | 3 | 7 | 8 | 6 | 6 | 8 | 7 | 3 | 2 | 7 | 7 | 3 |
| | | | | | | | | | 1 | 1 | 6 | 6 | | 2 | 7 | 7 | 6 | | | | | | 7 | 6 | |
| 20 | 8 | 7 | 7 | 7 | 2 | 8 | 7 | * | 5 | 8 | 6 | 7 | 5 | 5 | 9 | 9 | 8 | 8 | 7 | 8 | 6 | 3 | 7 | 8 | 5 |
| | | | | | | | | | 1 | 5 | 6 | 6 | 5 | 4 | 8 | 7 | 6 | 6 | 6 | 6 | 5 | | 7 | 7 | 5 |
| 21 | 8 | 8 | 9 | 6 | 7 | 8 | * | 4 | 5 | 8 | 7 | 9 | 7 | 8 | 9 | 9 | 9 | 9. | 8 | 9 | 7 | 8 | 8 | 8 | 7 |
| | | | | | | | | | 1 | 7 | 7 | 8 | 6 | 7 | 8 | 8 | 7 | 8 | 7 | 8 | 5 | 7 | 8 | 8 | 6 |
| 22 | 6 | 6 | 7 | 4 | 7 | 8 | 6 | 6 | 5 | 7 | 7 | 8 | 7 | 7 | 9 | 8 | 8 | 8 | 9 | 9 | 8 | 8 | 8 | 8 | 7 |
| | | | | | | | | | 1 | 6 | 7 | 8 | 6 | 7 | 8 | 8 | 7 | 6 | 7 | 7 | 5 | 6 | 8 | 8 | 6 |
| 23 | | | 5 | | | 6 | * | | 5 | 2 | | 8 | | 4 | 8 | 8 | 4 | 3 | | 7 | | | 7 | 7 | 4 |
| | | | | | | | | | 1 | | | 5 | | | 7 | 7 | 2 | | | | | | 7 | 4 | 4 |
| 24 | 4 | 5 | 6 | | | 6 | 5 | | 5 | 5 | 2 | 7 | | 5 | 8 | 8 | 6 | 7 | 5 | 7 | 3 | | 7 | 4 | 3 |
| | | | | | | | | | 1 | 2 | | 5 | | | 6 | 6 | 5 | 2 | | | 2 | | 6 | | |
| 25 | 8 | 7 | 8 | 7 | 7 | 8 | 7 | 6 | 5 | 8 | 7 | 9 | 8 | 7 | 9 | 9 | 8 | 8 | 9 | 9 | 7 | 8 | 7 | 8 | 6 |
| | | | | | | | | | 1 | 5 | 7 | 8 | 7 | 7 | 8 | 8 | 5 | 6 | 6 | 7 | 4 | 6 | 7 | 7 | 4 |
| 26 | 7 | 8 | 8 | 7 | 7 | 8 | 8 | 7 | 5 | 8 | 7 | 8 | 7 | 7 | 9 | 9 | 8 | 8 | 9 | 9 | 7 | 7 | 8 | 8 | 7 |
| | | | | | | | | | 1 | 7 | 7 | 8 | 7 | 7 | 8 | 8 | 6 | 6 | 8 | 8 | 7 | 6 | 7 | 7 | 6 |
| 27 | 8 | 8 | 8 | 7 | 6 | 7 | 8 | 7 | 5 | 8 | 7 | 9 | 7 | 8 | 9 | 9 | 8 | 9 | 9 | 9 | 7 | 7 | 7 | 8 | 9 |
| | | | | | | | | | 1 | 8 | 7 | 8 | 6 | 8 | 9 | 8 | 7 | 9 | 8 | 8 | 5 | 6 | 7 | 7 | 8 |
| 28 | 8 | 5 | 6 | 5 | 6 | 7 | 5 | 5 | 5 | 6 | 4 | 8 | 5 | 7 | 9 | 8 | 8 | 6 | 7 | 8 | 3 | 6 | 7 | 6 | 5 |
| | | | | | | | | | 1 | 5 | | 7 | 5 | 7 | 8 | 7 | 6 | 2 | 2 | 4 | 1 | 4 | 7 | 5 | 2 |
| 29 | 8 | 8 | 9 | 7 | 7 | 8 | 8 | 8 | 5 | 8 | 7 | 8 | 4 | 7 | 8 | 8 | 7 | 9 | 9 | 9 | 7 | 7 | 7 | 8 | 9 |
| | | | | | | | | | 1 | 7 | 5 | 8 | 4 | 7 | 8 | 7 | 7 | 8 | 8 | 9 | 5 | 5 | 7 | 8 | 4 |
| 30 | 6 | 7 | 6 | 5 | 7 | 7 | 7 | 4 | 5 | 5 | 7 | 8 | 6 | 6 | 8 | 8 | 7 | 7 | 8 | 7 | 7 | 7 | 7 | 7 | 4 |
| | | | | | | | | | 1 | 2 | 6 | 7 | 6 | 6 | 7 | 7 | 4 | 4 | 4 | 2 | 4 | 5 | 5 | 6 | 2 |
| 31 | 8 | 8 | 8 | 7 | 7 | 9 | 9 | 7 | 5 | 7 | 7 | 9 | 7 | 7 | 8 | 8 | 8 | 8 | 9 | 9 | 8 | 7 | 7 | 8 | 7 |
| | | | | | | | | | 1 | 6 | 7 | 8 | 7 | 7 | 7 | 7 | 7 | 7 | 8 | 8 | 7 | 6 | 7 | 7 | 6 |
| 32 | 6 | 8 | 7 | 4 | 7 | 7 | 7 | 6 | 5 | 7 | 8 | 8 | 7 | 7 | 8 | 9 | 7 | 8 | 9 | 9 | 8 | 8 | 7 | 8 | 8 |
| | | | | | | | | | 1 | 6 | 7 | 7 | 6 | 7 | 7 | 7 | 2 | 6 | 8 | 7 | 2 | 7 | 7 | 7 | 5 |
| 33 | 7 | 7 | 7 | 6 | 7 | 7 | 8 | 5 | 5 | 6 | 8 | 8 | 7 | 7 | 8 | 8 | 6 | 8 | 9 | 8 | 7 | 8 | 7 | 8 | 7 |
| | | | | | | | | | 1 | 5 | 8 | 8 | 6 | 7 | 7 | 7 | 3 | 6 | 8 | 6 | 2 | 7 | 7 | 8 | 4 |
| 34 | 5 | | 6 | 1 | 2 | 7 | 2 | 2 | 5 | 4 | 2 | 7 | 3 | 6 | 7 | 7 | | 7 | 6 | 7 | 4 | 6 | 7 | 7 | 6 |
| | | | | | | | | | 1 | 2 | | 3 | | 5 | 7 | 6 | | 2 | | 2 | | | 6 | 5 | |
| 35 | 6 | 8 | 8 | 6 | 4 | 7 | 6 | 4 | 5 | 6 | 7 | 7 | 6 | 6 | 9 | 9 | 5 | 7 | 9 | 8 | 8 | 6 | 7 | 8 | 8 |
| | | | | | | | | | 1 | 4 | 7 | 7 | 5 | 5 | 8 | 8 | 4 | 4 | 8 | 7 | 5 | | 7 | 7 | 7 |
| 36 | 6 | 5 | 8 | 2 | 7 | 9 | 8 | 5 | 5 | 6 | 8 | 7 | 7 | 7 | 8 | 8 | 8 | 8 | 9 | 8 | 7 | 8 | 7 | 8 | 8 |
| | | | | | | | | | 1 | 5 | 8 | 7 | 2 | 7 | 7 | 7 | 2 | 2 | 2 | 7 | 2 | 7 | 7 | 7 | 2 |
| 37 | 7 | 7 | 8 | 7 | 3 | 7 | 7 | 7 | 5 | 7 | 7 | 7 | 5 | 6 | 8 | 8 | 7 | 7 | 9 | 8 | 7 | 4 | 7 | 7 | 7 |
| | | | | | | | | | 1 | 5 | 7 | 7 | 5 | 5 | 7 | 7 | 2 | 5 | 6 | 7 | 2 | | 7 | 7 | 2 |
| 38 | 7 | 7 | 7 | 7 | 7 | 7 | 7 | 8 | 5 | 6 | 6 | 8 | 6 | 7 | 8 | 7 | 8 | 8 | 9 | 9 | 8 | 7 | 6 | 7 | 7 | 8 |
| | | | | | | | | | 1 | 5 | 5 | 7 | 4 | 7 | 7 | 7 | 7 | 6 | 2 | 6, | 4 | 6 | 7 | 7 | 8 |
| 39 | 7 | 7 | 8 | 7 | 7 | 7 | 6 | 5 | 5 | 7 | 3 | 8 | 3 | 7 | 7 | 7 | 4 | 8 | 8 | 8 | 3 | 4 | 7 | 7 | 6 |
| | | | | | | | | | 1 | 2 | 1 | 7 | 1 | 6 | 7 | 7 | 2 | 5 | 2 | 5 | 1 | | 6 | 6 | 5 |
| 40 | 5 | 6 | 6 | 7 | | 7 | 8 | | 5 | 6 | 6 | 7 | 4 | 6 | 8 | 9 | 6 | 7 | 9 | 8 | 7 | 6 | 7 | 7 | 8 |
| | | | | | | | | | 1 | 3 | 2 | 6 | 2 | 3 | 7 | 8 | 2 | 5 | 7 | 7 | 5 | 4 | 7 | 7 | 6 |
| 41 | 7 | 8 | 7 | 7 | 6 | 7 | 7 | 8 | 5 | 7 | 8 | 8 | 7 | 7 | 8 | 9 | 7 | 8 | 9 | 9 | 8 | 8 | 7 | 7 | 8 |
| | | | | | | | | | 1 | 6 | 7 | 7 | 7 | 7 | 7 | 9 | 6 | 7 | 9 | 7 | 7 | 7 | 7 | 7 | 6 |
| 42 | 6 | 8 | 7 | 7 | 7 | 7 | 7 | 6 | 5 | 6 | 7 | 7 | 7 | 7 | 8 | 7 | 7 | 8 | 9 | 8 | 7 | 8 | 7 | 8 | 8 |
| | | | | | | | | | 1 | | 4 | 2 | 4 | 5 | 7 | 7 | 6 | 7 | 7 | 7 | 6 | 7 | 7 | 7 | 6 |
| 43 | 7 | 7 | 7 | 7 | 7 | 7 | 7 | 7 | 5 | 8 | 8 | 8 | 7 | 7 | 8 | 9 | 7 | 8 | 9 | 8 | 7 | 8 | 7 | 8 | 9 |

TABLE IV-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 44 | 4 | 2 | 6 | 2 | 3 | 8 | 2 | 6 | 1 | 7 | 7 | 7 | 6 | 7 | 8 | 8 | 6 | 7 | 7 | 7 | 6 | 7 | 7 | 7 | 8 |
| | | | | | | | | | 5 | 4 | 3 | 7 | 2 | 7 | 8 | 7 | 7 | 4 | 7 | 7 | 4 | 6 | 7 | 7 | 6 |
| | | | | | | | | | 1 | 2 | 1 | 5 | | 6 | 7 | 6 | 4 | 2 | | 5 | 2 | 3 | 7 | 7 | 2 |
| 45 | 5 | 7 | 7 | 5 | 5 | 7 | 7 | 6 | 5 | 6 | 7 | 8 | 4 | 7 | 8 | 7 | 7 | 7 | 8 | 8 | 7 | 7 | 7 | 7 | 9 |
| | | | | | | | | | 1 | 4 | 2 | 7 | 2 | 4 | 7 | 7 | 5 | 5 | 6 | 7 | 4 | 2 | 7 | 7 | 6 |
| 46 | 6 | 7 | 7 | 7 | | 9 | 7 | | 5 | 7 | 7 | 7 | 7 | 6 | 8 | 8 | 6 | 8 | 8 | 8 | 7 | 6 | 7 | 7 | 6 |
| | | | | | | | | | 1 | 2 | 6 | 7 | 6 | 2 | 7 | 7 | 5 | 7 | 7 | 6 | 4 | | 7 | 7 | 5 |
| 47 | 5 | 7 | 6 | 2 | | 7 | 6 | 6 | 5 | 4 | | 6 | | 5 | 8 | 8 | 5 | 7 | 7 | 7 | 7 | | 7 | 7 | 8 |
| | | | | | | | | | 1 | | | 2 | | | 7 | 7 | 4 | 4 | | 5 | 2 | | 6 | 7 | 7 |
| 48 | | | 4 | | 3 | 7 | | | 5 | 4 | | 7 | 2 | 7 | 8 | 8 | 5 | 5 | | 6 | | | 7 | | |
| | | | | | | | | | 1 | 2 | | 3 | | 6 | 7 | 7 | | 2 | | | | | 6 | | |
| 49 | 8 | 8 | 8 | 8 | 7 | 8 | 8 | 7 | 5 | 6 | 8 | 8 | 7 | 7 | 8 | 8 | 7 | 9 | 9 | 9 | 8 | 9 | 8 | 8 | 8 |
| | | | | | | | | | 1 | 3 | 7 | 8 | 6 | 7 | 7 | 7 | 5 | 7 | 8 | 8 | 7 | 8 | 8 | 8 | 7 |
| 50 | * | * | * | * | * | * | * | * | 5 | 7 | 7 | 8 | 6 | 7 | 8 | 8 | 7 | 8 | 8 | 9 | 8 | 8 | 8 | 8 | 7 |
| | | | | | | | | | 1 | 4 | 3 | 8 | 4 | 7 | 7 | 8 | 5 | 8 | 6 | 8 | 6 | 6 | 8 | 8 | 5 |
| 51 | 8 | 8 | 8 | 7 | 6 | 8 | 8 | 7 | 5 | 8 | 8 | 8 | 7 | 7 | 8 | 8 | 7 | 9 | 9 | 9 | 8 | 7 | 8 | 8 | 8 |
| | | | | | | | | | 1 | 6 | 8 | 8 | 6 | 7 | 7 | 7 | 5 | 5 | 9 | 7 | 5 | 4 | 8 | 8 | 3 |
| 52 | 7 | 8 | 7 | 4 | 2 | 8 | 8 | 5 | 5 | 5 | 6 | 8 | 2 | 5 | 8 | 8 | 5 | 8 | 8 | 9 | 6 | 7 | 7 | 8 | 8 |
| | | | | | | | | | 1 | 3 | 5 | 8 | | 3 | 6 | 7 | 2 | 3 | 3 | 6 | 5 | 2 | 7 | 8 | 5 |
| 53 | 8 | 7 | 8 | 7 | | 8 | 8 | 6 | 5 | 6 | 6 | 8 | 5 | 3 | 8 | 8 | 5 | 8 | 8 | 9 | 8 | 5 | 8 | 8 | 6 |
| | | | | | | | | | 1 | 4 | 2 | 8 | 2 | | 7 | 7 | 2 | 6 | 7 | 8 | 7 | 2 | 8 | 8 | 5 |
| 54 | 8 | 8 | 8 | 8 | 6 | 8 | 8 | 6 | 5 | 7 | 8 | 8 | 8 | 7 | 8 | 8 | 6 | 9 | 9 | 9 | 8 | 8 | 8 | 8 | 8 |
| | | | | | | | | | 1 | 4 | 7 | 8 | 7 | 7 | 7 | 7 | 4 | 6 | 9 | 7 | 7 | 5 | 8 | 8 | 6 |
| 55 | 8 | 7 | 7 | 7 | | 8 | 8 | | 5 | 5 | 4 | 8 | | 2 | 8 | 8 | 5 | 7 | 8 | 9 | 7 | | 8 | 8 | 5 |
| | | | | | | | | | 1 | 1 | 2 | 7 | | | 7 | 7 | | 3 | 7 | 7 | 4 | | 8 | 7 | |
| 56 | 5 | | 7 | 6 | 5 | 7 | 6 | 5 | 5 | 7 | 2 | 8 | 5 | 7 | 8 | 8 | 5 | 8 | 6 | 8 | 7 | 7 | 7 | 7 | 7 |
| | | | | | | | | | 1 | 5 | 1 | 7 | 4 | 7 | 7 | 7 | 2 | 7 | 2 | 7 | 2 | 5 | 7 | 7 | 5 |
| 57 | 4 | | 7 | | 6 | 7 | 6 | | 5 | 6 | | 7 | 4 | 7 | 7 | 7 | 3 | 7 | 7 | 7 | 4 | 7 | 7 | 7 | 4 |
| | | | | | | | | | 1 | 4 | | 5 | 2 | 6 | 7 | 7 | 2 | 5 | 2 | 6 | 2 | 6 | 7 | 7 | |
| 58 | 6 | 7 | 7 | 6 | 5 | 7 | 6 | 7 | 5 | 6 | 7 | 7 | 6 | 6 | 7 | 7 | 6 | 8 | 9 | 8 | 7 | 7 | 7 | 7 | 7 |
| | | | | | | | | | 1 | 4 | 6 | 7 | 5 | 6 | 6 | 7 | 2 | 6 | 8 | 7 | 6 | 2 | 7 | 7 | 5 |
| 59 | 6 | 7 | 7 | 6 | 4 | 7 | 4 | 5 | 5 | 6 | 7 | 7 | 5 | 7 | 7 | 7 | 4 | 8 | 9 | 8 | 7 | 7 | 7 | 7 | 7 |
| | | | | | | | | | 1 | 2 | 6 | 7 | 2 | 6 | 7 | 7 | 2 | 4 | 7 | 7 | 6 | | 6 | 7 | 2 |
| 60 | 7 | 6 | 7 | 7 | | 7 | 7 | | 5 | 5 | 4 | 7 | 4 | 7 | 8 | 8 | 4 | 7 | 7 | 7 | 7 | 6 | 7 | 7 | 4 |
| | | | | | | | | | 1 | 2 | 2 | 7 | 2 | | 7 | 7 | 2 | 6. | 5 | 5 | 2 | | 7 | 7 | 2 |
| 61 | 7 | 8 | 8 | 6 | 7 | 8 | 8 | 7 | 5 | 6 | 7 | 8 | 6 | 7 | 8 | 8 | 9 | 8 | 9 | 9 | 7 | 8 | 7 | 7 | 8 |
| | | | | | | | | | 1 | 4 | 5 | 8 | 2 | 7 | 7 | 7 | 8 | 7 | 7 | 7 | 4 | 7 | 7 | 7 | 8 |
| 62 | 7 | 8 | 8 | 7 | 7 | 7 | 7 | 8 | 5 | 7 | 7 | 7 | 7 | 7 | 7 | 7 | 8 | 9 | 9 | 9 | 8 | 8 | 7 | 7 | 8 |
| | | | | | | | | | 1 | 6 | 7 | 7 | 6 | 7 | 7 | 7 | 7 | 8 | 8 | 8 | 6 | 7 | 7 | 7 | 8 |
| 63 | 7 | 8 | 8 | 7 | 5 | 7 | 7 | 6 | 5 | 8 | 8 | 7 | 5 | 7 | 8 | 8 | 7 | 8 | 9 | 8 | 7 | 7 | 7 | 7 | 8 |
| | | | | | | | | | 1 | 7 | 7 | 7 | 2 | 7 | 7 | 7 | 6 | 6 | 9 | 7 | 7 | 7 | 7 | 7 | 6 |
| 64 | 7 | 6 | 7 | 7 | | 7 | 7 | | 5 | 5 | 4 | 7 | 4 | 7 | 8 | 8 | 4 | 7 | 7 | 7 | 7 | 6 | 7 | 7 | 4 |
| | | | | | | | | | 1 | 2 | 2 | 7 | 2 | | 7 | 7 | 2 | 6 | 5 | 5 | 2 | | 7 | 7 | 2 |
| 65 | 7 | 8 | 7 | 7 | 7 | 7 | 6 | 7 | 5 | 8 | 8 | 8 | 7 | 7 | 8 | 8 | 8 | 8 | 9 | 8 | 8 | 8 | 7 | 7 | 8 |
| | | | | | | | | | 1 | 5 | 8 | 7 | 6 | 7 | 7 | 7 | 8 | 6 | 9 | 7 | 7 | 6 | 7 | 6 | |
| 66 | 7 | 8 | 8 | 7 | 7 | 7 | 7 | 7 | 5 | 7 | 8 | 8 | 7 | 7 | 8 | 8 | 8 | 8 | 9 | 9 | 8 | 8 | 8 | 8 | 9 |
| | | | | | | | | | 1 | 5 | 8 | 7 | 6 | 7 | 7 | 7 | 8 | 7 | 8 | 8 | 2 | 7 | 7 | 7 | 2 |
| 67 | 7 | 6 | 7 | 7 | 7 | 7 | 7 | 7 | 5 | 8 | 7 | 9 | 7 | 7 | 8 | 8 | 8 | 9 | 9 | 9 | 7 | 8 | 7 | 8 | 8 |
| | | | | | | | | | 1 | 7 | 2 | 8 | 5 | 7 | 7 | 7 | 7 | 8 | 4 | 8 | 2 | 7 | 7 | 7 | 2 |
| 68 | 6 | 6 | 5 | 6 | 6 | 7 | 6 | 5 | 5 | 7 | 7 | 8 | 7 | 8 | 8 | 9 | 7 | 8 | 8 | 7 | 7 | 7 | 7 | 7 | 7 |
| | | | | | | | | | 1 | 5 | | 7 | 4 | 7 | 8 | 7 | 5 | 7 | 6 | 6 | 5 | | 7 | 6 | 4 |
| 69 | 7 | 7 | 7 | 6 | 5 | 7 | 7 | 6 | 5 | 6 | 7 | 8 | 6 | 7 | 8 | 8 | 8 | 7 | 9 | 8 | 6 | 7 | 7 | 8 | 8 |
| | | | | | | | | | 1 | 4 | 2 | 7 | 4 | 7 | 8 | 7 | 6 | 6 | 6 | 6 | 5 | | 7 | 7 | 2 |
| 70 | 7 | 8 | 7 | 6 | 6 | 7 | 8 | 6 | 5 | 7 | 7 | 8 | 7 | 7 | 7 | 8 | 7 | 8 | 9 | 8 | 7 | 7 | 7 | 8 | 8 |
| | | | | | | | | | 1 | 5 | 7 | 7 | 7 | 7 | 7 | 7 | 6 | 6 | 8 | 7 | 5 | 2 | 7 | 7 | 7 |
| 71 | 5 | 8 | 7 | 2 | 2 | 7 | 4 | 2 | 5 | 3 | 7 | 8 | 6 | 7 | 7 | 7 | 5 | 5 | 9 | 8 | 4 | 6 | 7 | 8 | 4 |
| | | | | | | | | | 1 | | 2 | 7 | 5 | 6 | 7 | 7 | 2 | 2 | 6 | 6 | 2 | 2 | 7 | 7 | 2 |
| 72 | 7 | 8 | 7 | 7 | 6 | 7 | 7 | 4 | 5 | 7 | 8 | 8 | 7 | 7 | 7 | 8 | 6 | 8 | 9 | 9 | 6 | 7 | 7 | 8 | 7 |
| | | | | | | | | | 1 | 4 | 8 | 8 | 5 | 6 | 7 | 7 | 6 | 7 | 9 | 8 | 5 | 6 | 7 | 7 | 5 |
| 73 | 6 | 7 | 7 | 4 | 7 | 7 | 7 | 5 | 5 | 5 | 7 | 7 | 4 | 7 | 7 | 7 | 6 | 6 | 9 | 4 | 5 | 8 | 7 | 4 | 5 |
| | | | | | | | | | 1 | * | * | * | * | * | * | * | * | * | * | * | * | * | * | * | * |
| 74 | 8 | 4 | 8 | 7 | 4 | 7 | 7 | 5 | 5 | 8 | 5 | 8 | 4 | 7 | 7 | 8 | 7 | 8 | 8 | 8 | 8 | 7 | 7 | 8 | 7 |
| | | | | | | | | | 1 | 6 | 4 | 8 | 2 | 7 | 7 | 7 | 6 | 6 | 7 | 7 | 6 | 4 | 7 | 7 | 6 |
| 75 | 7 | 7 | 8 | 7 | 4 | 7 | 7 | 4 | 5 | 8 | 6 | 8 | 7 | 7 | 8 | 8 | 7 | 8 | 9 | 8 | 8 | 4 | 7 | 7 | 5 |
| | | | | | | | | | 1 | 6 | 5 | 8 | 6 | 6 | 7 | 7 | 5 | 6 | 8 | 7 | 6 | | 7 | 8 | 4 |
| 76 | 5 | 2 | 7 | 6 | 4 | 7 | 8 | 5 | 5 | 6 | | 8 | 1 | 6 | 8 | 8 | 4 | 7 | 7 | 8 | 4 | 2 | 7 | 7 | 7 |
| | | | | | | | | | 1 | 2 | | 7 | | 4 | 7 | 7 | 2 | 5 | 5 | 7 | 2 | | 7 | 7 | 4 |
| 77 | 5 | 2 | 7 | 2 | 3 | 6 | 7 | 4 | 5 | 6 | 1 | 8 | 4 | 4 | 8 | 8 | 4 | 6 | 7 | 7 | 2 | 2 | 7 | 8 | 4 |
| | | | | | | | | | 1 | 2 | | 7 | | 2 | 7 | 7 | 2 | 5 | 4 | 6 | | | 7 | 7 | 2 |
| 78 | 7 | 6 | 7 | 6 | | 7 | 7 | 6 | 5 | 5 | 6 | 7 | 5 | 6 | 7 | 7 | 2 | 7 | 8 | 7 | 5 | | 7 | 8 | 6 |
| | | | | | | | | | 1 | 2 | 6 | 6 | 2 | 7 | 7 | | | 6 | 7 | 7 | 2 | | 7 | 8 | 2 |
| 79 | 7 | 6 | 7 | 6 | 7 | 8 | 7 | 7 | 5 | 6 | 4 | 7 | 4 | 7 | 9 | 9 | 6 | 8 | 9 | 8 | 7 | 7 | 8 | 8 | 8 |
| | | | | | | | | | 1 | 4 | 2 | 7 | 2 | 7 | 8 | 9 | 5 | 7 | 8 | 6 | 4 | 2 | 7 | 8 | 8 |
| 80 | 7 | 6 | 7 | 4 | 5 | 7 | 7 | 7 | 5 | 7 | 6 | 7 | 6 | 7 | 7 | 8 | 6 | 7 | 9 | 8 | 6 | 4 | 7 | 8 | 8 |
| | | | | | | | | | 1 | 6 | 5 | 7 | 5 | 6 | 7 | 7 | 4 | 5 | 9 | 7 | 2 | | 7 | 8 | 8 |
| 81 | 6 | 5 | 7 | 2 | | 7 | 7 | 6 | 5 | 6 | 4 | 8 | 4 | 5 | 7 | 8 | 6 | 7 | 7 | 8 | 6 | 5 | 7 | 7 | 8 |
| | | | | | | | | | 1 | 2 | 4 | 7 | 2 | 2 | 7 | 7 | 2 | 5 | 2 | 7 | | | 7 | 7 | 6 |
| 82 | 7 | 6 | 7 | 6 | 5 | 7 | 7 | 6 | 5 | 6 | 5 | 7 | 4 | 7 | 9 | 9 | 5 | 7 | 9 | 7 | 4 | | 7 | 8 | 8 |
| | | | | | | | | | 1 | 4 | 5 | 6 | 2 | 6 | 8 | 8 | 2 | 5 | 6 | 4 | 2 | | 7 | 8 | 7 |

TABLE IV-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 83 | 7 | 5 | 6 | 7 | | 9 | 7 | 6 | 5 | 7 | 4 | 7 | 4 | 5 | 9 | 8 | 6 | 8 | 9 | 9 | 7 | | 7 | 8 | 7 |
| | | | | | | | | | 1 | 5 | 2 | 6 | 2 | | 8 | 8 | 5 | 7 | 8 | 7 | 6 | | 7 | 7 | 6 |
| 84 | 8 | 6 | 8 | 8 | 7 | 6 | 6 | 7 | 5 | 8 | 6 | 8 | 8 | 7 | 8 | 8 | 8 | 8 | 9 | 8 | 8 | 8 | 8 | 8 | 6 |
| | | | | | | | | | 1 | 7 | 6 | 8 | 7 | 6 | 8 | 8 | 7 | 7 | 9 | 8 | 7 | 6 | 8 | 7 | 2 |
| 85 | 8 | 6 | 8 | 8 | 7 | 8 | 8 | 6 | 5 | 7 | 6 | 8 | 7 | 7 | 8 | 8 | 8 | 8 | 9 | 8 | 8 | 8 | 8 | 8 | 7 |
| | | | | | | | | | 1 | 6 | 6 | 7 | 5 | 6 | 7 | 7 | 8 | 7 | 7 | 8 | 6 | 6 | 7 | 7 | 5 |
| 86 | 7 | 2 | 7 | 4 | 6 | 7 | 6 | 6 | 5 | 5 | 5 | 7 | 2 | 6 | 8 | 7 | 7 | 7 | 8 | 8 | 7 | 5 | 8 | 7 | 1 |
| | | | | | | | | | 1 | 2 | 2 | 6 | | 5 | 7 | 6 | 6 | 2 | 1 | 2 | 1 | 1 | 7 | 5 | 1 |
| 87 | 3 | 4 | 2 | 3 | | 7 | 6 | | 5 | 4 | 3 | 7 | 4 | | 7 | 8 | 4 | 7 | 7 | 8 | 6 | 4 | 7 | 7 | |
| | | | | | | | | | 1 | 2 | | 5 | 2 | | 7 | 7 | 2 | 5 | 6 | 6 | 5 | 2 | 7 | 7 | |
| 88 | 6 | 7 | 6 | 5 | 2 | 7 | 6 | 2 | 5 | 6 | 5 | 7 | 6 | 4 | 7 | 7 | 4 | 7 | 9 | 8 | 7 | 6 | 7 | 8 | 6 |
| | | | | | | | | | 1 | 2 | 5 | 7 | 2 | 2 | 7 | 7 | 2 | 6 | 8 | 7 | 7 | 2 | 7 | 8 | 5 |
| 89 | 6 | 4 | 6 | 7 | 2 | 7 | 6 | 4 | 5 | 6 | 5 | 8 | 7 | | 8 | 7 | 5 | 8 | 8 | 8 | 8 | 6 | 7 | 8 | 7 |
| | | | | | | | | | 1 | 2 | 2 | 7 | 2 | | 7 | 6 | 4 | 7 | 7 | 7 | 7 | | 7 | 7 | 6 |
| 90 | 3 | 2 | 7 | 6 | | 7 | 6 | | 5 | 4 | 6 | 7 | 4 | 2 | 8 | 8 | 4 | 7 | 8 | 8 | 8 | 4 | 7 | 7 | |
| | | | | | | | | | 1 | 2 | 2 | 5 | 2 | | 7 | 6 | 2 | 6 | 7 | 7 | 8 | | 7 | 6 | |
| 91 | 2 | | 4 | | | 7 | 2 | 2 | 5 | 7 | 7 | 7 | 7 | 7 | 8 | 8 | 7 | 7 | 9 | 7 | 6 | 8 | 7 | 7 | 8 |
| | | | | | | | | | 1 | 4 | 6 | 6 | 6 | 5 | 6 | 7 | 8 | 7 | 6 | 6 | 5 | 2 | 6 | 7 | 7 | 8 |
| 92 | 3 | 4 | 6 | 3 | 4 | 7 | 7 | 5 | 5 | 4 | 3 | 7 | 4 | 7 | 8 | 7 | 6 | 5 | 6 | 6 | 5 | 6 | 7 | 7 | 4 |
| | | | | | | | | | 1 | 2 | 2 | 6 | 2 | 6 | 7 | 7 | 5 | 1 | 2 | 2 | 2 | 2 | 6 | 6 | 2 |
| 93 | 7 | 6 | 5 | 4 | 7 | 6 | 5 | 6 | 5 | 2 | 4 | 7 | 3 | 7 | 8 | 8 | 6 | 7 | 6 | 5 | 6 | 7 | 7 | 7 | 4 |
| | | | | | | | | | 1 | | 2 | 5 | | 6 | 7 | 7 | 4 | 4 | | 2 | 2 | 6 | 6 | 6 | 2 |
| 94 | 5 | 6 | 4 | 1 | 1 | 7 | 7 | 5 | 5 | 4 | 7 | 8 | 7 | 7 | 8 | 8 | 6 | 7 | 8 | 8 | 4 | 5 | 7 | 7 | 4 |
| | | | | | | | | | 1 | 2 | 6 | 7 | 2 | 6 | 7 | 8 | 5 | 4 | 6 | 6 | 2 | 2 | 7 | 6 | 3 |
| 95 | 6 | 4 | 4 | 4 | 7 | 7 | 7 | 4 | 5 | 5 | 4 | 7 | 4 | 7 | 8 | 8 | 6 | 4 | 6 | 7 | 6 | 6 | 7 | 7 | 4 |
| | | | | | | | | | 1 | 1 | 2 | 6 | | | 7 | 8 | 7 | 4 | 2 | 5 | 2 | 5 | 2 | 6 | 7 | |
| 96 | 3 | 2 | 4 | 2 | 3 | 6 | 6 | 4 | 5 | 7 | 5 | 7 | 7 | 7 | 7 | 8 | 6 | 7 | 6 | 4 | 4 | 5 | 7 | 7 | 5 |
| | | | | | | | | | 1 | 2 | 2 | 4 | 2 | 6 | 7 | 7 | 5 | 2 | 2 | 2 | | 2 | 7 | 7 | 4 |
| 97 | 7 | 7 | 6 | 5 | 6 | 7 | 7 | 5 | 5 | 7 | 6 | 7 | 7 | 7 | 8 | 9 | 5 | 9 | 9 | 8 | 8 | 7 | 7 | 7 | 5 |
| | | | | | | | | | 1 | 5 | 5 | 6 | 5 | 6 | 7 | 8 | 4 | 7 | 8 | 6 | 6 | 6 | 7 | 6 | 2 |
| 98 | 7 | 8 | 7 | 6 | 6 | 7 | 8 | 6 | 5 | 7 | 7 | 8 | 7 | 7 | 8 | 9 | 7 | 8 | 9 | 8 | 8 | 7 | 7 | 8 | 8 |
| | | | | | | | | | 1 | 6 | 7 | 8 | 5 | 6 | 7 | 8 | 6 | 7 | 8 | 7 | 5 | 6 | 7 | 7 | 6 |
| 99 | * | * | * | * | * | * | * | * | 5 | 6 | 4 | 7 | 5 | 2 | 8 | 9 | 6 | 7 | 8 | 6 | 6 | | 7 | 8 | 7 |
| | | | | | | | | | 1 | 4 | 2 | 6 | 2 | | 8 | 8 | 6 | 5 | 7 | 7 | 2 | | 7 | 7 | 2 |
| 100 | 7 | 6 | 7 | 7 | 6 | 6 | 7 | 5 | 5 | 7 | 6 | 8 | 6 | 7 | 8 | 8 | 5 | 8 | 9 | 8 | 7 | 7 | 7 | 7 | 8 |
| | | | | | | | | | 1 | 6 | 6 | 7 | 4 | 7 | 7 | 7 | 4 | 6 | 9 | 7 | 6 | 6 | 7 | 7 | 7 |
| 101 | 7 | 6 | 7 | 6 | | 7 | 6 | 5 | 5 | 7 | 5 | 8 | 4 | 1 | 8 | 8 | 7 | 8 | 8 | 8 | 8 | | 7 | 7 | 7 |
| | | | | | | | | | 1 | 4 | 4 | 7 | 2 | | 7 | 7 | 5 | 6 | 7 | 6 | 6 | | 7 | 7 | 2 |
| 102 | 7 | 7 | 6 | 6 | | 8 | 6 | 5 | 5 | 7 | 6 | 7 | 4 | 3 | 8 | 8 | 6 | 7 | 9 | 9 | 6 | 4 | 7 | 7 | 5 |
| | | | | | | | | | 1 | 2 | 2 | 7 | 2 | 1 | 7 | 7 | 5 | 6 | 2 | 6 | 5 | | 6 | 5 | |
| 103 | 7 | 2 | 6 | 7 | | 9 | 7 | 3 | 5 | 4 | 3 | 7 | 3 | | 9 | 8 | 5 | 6 | 2 | 8 | 7 | 5 | 7 | 7 | 2 |
| | | | | | | | | | 1 | 2 | | 5 | | | 8 | 6 | 4 | 2 | | 6 | 6 | 2 | 5 | 5 | |
| 104 | 6 | 7 | 6 | 6 | 2 | 7 | 7 | 2 | 5 | 6 | 7 | 7 | 5 | 5 | 7 | 7 | 6 | 5 | 6 | 6 | 7 | 6 | 8 | 7 | 2 |
| | | | | | | | | | 1 | 2 | 6 | 7 | 2 | 5 | 7 | 6 | 4 | 2 | 5 | 5 | 7 | 2 | 7 | 7 | |
| 105 | 7 | 7 | 7 | 7 | 5 | 8 | 7 | 7 | 5 | 8 | 7 | 8 | 8 | 6 | 8 | 8 | 8 | 8 | 9 | 8 | 7 | 8 | 8 | 8 | 5 |
| | | | | | | | | | 1 | 5 | 7 | 8 | 7 | 2 | 7 | 7 | 6 | 7 | 8 | 5 | 6 | 5 | 8 | 7 | 2 |
| 106 | 6 | 7 | 7 | 4 | 7 | 8 | 7 | 6 | 5 | 6 | 7 | 7 | 4 | 6 | 8 | 8 | 4 | 8 | 9 | 7 | 7 | 8 | 8 | 8 | 8 |
| | | | | | | | | | 1 | 5 | 6 | 5 | 2 | 6 | 7 | 7 | 2 | 6 | 7 | 6 | 6 | 7 | 8 | 7 | 6 |
| 107 | 7 | 4 | 7 | 2 | 4 | 7 | 6 | 4 | 5 | 3 | 6 | 6 | 4 | 6 | 8 | 8 | 7 | 4 | 7 | 8 | 2 | 2 | 7 | 8 | 2 |
| | | | | | | | | | 1 | 1 | 2 | 6 | | 5 | 8 | 7 | 2 | 2 | 2 | 4 | | | 6 | 8 | |
| 108 | 3 | 7 | 6 | 2 | 2 | 8 | 7 | 2 | 5 | 4 | 7 | 7 | 2 | 4 | 9 | 8 | 4 | 7 | 7 | 6 | 4 | | 7 | 8 | 2 |
| | | | | | | | | | 1 | 2 | 7 | 7 | | | 8 | 7 | | 4 | 6 | 6 | | | 5 | 7 | |
| 109 | 7 | 7 | 6 | 7 | 4 | 8 | 7 | 6 | 5 | 7 | 6 | 8 | 7 | 6 | 9 | 9 | 8 | 8 | 9 | 8 | 8 | 7 | 8 | 8 | 8 |
| | | | | | | | | | 1 | 6 | 5 | 7 | 7 | 5 | 8 | 8 | 7 | 7 | 9 | 7 | 6 | 6 | 7 | 7 | 4 |
| 110 | 8 | 8 | 4 | 3 | 8 | 9 | 9 | 8 | 5 | 6 | 7 | 7 | 7 | 8 | 9 | 9 | 7 | 4 | * | 7 | 4 | 8 | 8 | 8 | 8 |
| | | | | | | | | | 1 | 1 | 6 | 7 | 5 | 8 | 9 | 8 | 6 | | 2 | 3 | | 6 | 8 | 8 | 6 |
| 111 | 7 | 8 | 8 | 7 | 7 | 8 | 8 | 7 | 5 | 7 | 8 | 8 | 6 | 8 | 9 | 9 | 9 | 7 | 9 | 8 | 7 | 7 | 8 | 8 | 8 |
| | | | | | | | | | 1 | 5 | 8 | 8 | 5 | 7 | 8 | 8 | 8 | 2 | 8 | 6 | 6 | 2 | 7 | 7 | 2 |
| 112 | 7 | 8 | 6 | 4 | 6 | 7 | 4 | 5 | 5 | 7 | 4 | 7 | 7 | 7 | 8 | 8 | 4 | 7 | 8 | 6 | 4 | 3 | 5 | 6 | 4 |
| | | | | | | | | | 1 | 6 | 2 | 7 | 5 | 7 | 8 | 7 | 2 | 2 | 7 | 2 | 2 | | 2 | 5 | 2 |
| 113 | 7 | 6 | 4 | 3 | 2 | 7 | 5 | 4 | 5 | 7 | 6 | 8 | 5 | 7 | 8 | 8 | 6 | 8 | 8 | 6 | 4 | 2 | 7 | 8 | 2 |
| | | | | | | | | | 1 | 4 | 5 | 7 | 4 | 6 | 8 | 8 | 5 | 2 | 7 | 4 | 2 | | 6 | 7 | |
| 114 | | | | | | | | | 5 | | | | | | 4 | 6 | 4 | 5 | | | | | | | | |
| | | | | | | | | | 1 | | | | | | 2 | 2 | 2 | 4 | | | | | | | | |
| 115 | 6 | 8 | 6 | 7 | | 8 | 8 | 6 | 5 | 4 | 7 | 7 | 2 | 4 | 9 | 8 | 6 | 4 | 8 | 8 | 4 | | 8 | 8 | 4 |
| | | | | | | | | | 1 | 2 | 6 | 7 | | 2 | 8 | 8 | 5 | 2 | 7 | 8 | 2 | | 8 | 8 | 2 |
| 116 | 7 | 8 | 6 | 5 | | 8 | 6 | 4 | 5 | 7 | 6 | 7 | 4 | 4 | 8 | 8 | 4 | 6 | 8 | 7 | 6 | 4 | 7 | 8 | 5 |
| | | | | | | | | | 1 | 2 | 5 | 7 | 2 | 2 | 7 | 7 | 2 | 5 | 6 | 6 | 2 | 2 | 6 | 7 | 4 |
| 117 | 7 | 6 | 6 | 4 | | 6 | 6 | 5 | 5 | 3 | 4 | 7 | 4 | | 8 | 8 | 6 | 6 | 7 | 6 | 2 | | 6 | 8 | 6 |
| | | | | | | | | | 1 | 1 | 2 | 6 | 2 | | 7 | 7 | 4 | 5 | 2 | 5 | | | 5 | 7 | 5 |
| 118 | 7 | 6 | 7 | 6 | 5 | 7 | 6 | 7 | 5 | 7 | 7 | 8 | 6 | 7 | 7 | 8 | 6 | 7 | 8 | 6 | 4 | 6 | 8 | 8 | 5 |
| | | | | | | | | | 1 | 4 | 7 | 8 | 2 | 2 | 6 | 8 | 5 | 2 | 7 | 5 | 2 | 2 | 7 | 7 | 4 |
| 119 | 7 | 8 | 7 | 7 | 7 | 8 | 8 | 8 | 5 | 8 | 8 | 8 | 7 | 8 | 8 | 8 | 8 | 8 | 9 | 8 | 4 | 8 | 8 | 8 | 7 |
| | | | | | | | | | 1 | 7 | 8 | 8 | 6 | 7 | 8 | 8 | 7 | 7 | 7 | 2 | 2 | | 8 | 7 | 4 |
| 120 | | | | | 2 | 8 | 7 | | 5 | | | | | | | | | | | | | | | | |
| | | | | | | | | | 1 | | | | | | | | | | | | | | | | |
| 121 | | | | | 8 | 4 | | | 5 | | | | | | 7 | 7 | 2 | | | | | | 7 | | |
| | | | | | | | | | 1 | | | | | | 6 | 5 | | | | | | | 7 | | |
| 122 | 7 | 8 | 7 | 7 | 4 | 8 | 7 | 6 | 5 | 7 | 8 | 8 | 7 | 7 | 8 | 8 | 8 | 4 | 8 | 7 | 6 | 4 | 8 | 8 | 2 |

TABLE IV-continued

| Compound of Ex. No. | Soil drench 10 kg/ha Mz | R | BG | O | L | M | SB | S | Dosage kg/ha | Foliar spray Mz | R | BG | O | L | M | SB | S | Pre-emergence Mz | R | BG | O | L | M | SB | S |
|---|---|---|---|---|---|---|---|---|---|---|---|---|---|---|---|---|---|---|---|---|---|---|---|---|---|
| 123 | 7 | 8 | 8 | 7 | 7 | 8 | 8 | 7 | 1 | 5 | 8 | 8 | 6 | 5 | 8 | 8 | 7 | 2 | 8 | 4 | 5 |   | 8 | 7 |   |
|   |   |   |   |   |   |   |   |   | 5 | 6 | 7 | 8 | 7 | 7 | 8 | 9 | 7 | 8 | 9 | 7 | 6 | 8 | 8 | 8 | 6 |
| 124 | 4 | 7 | 7 | 4 |   | 7 | 6 | 7 | 1 | 5 | 7 | 8 | 6 | 6 | 7 | 8 | 6 | 4 | 8 | 6 | 5 | 2 | 8 | 7 | 5 |
|   |   |   |   |   |   |   |   |   | 5 | 2 | 6 | 6 |   |   | 8 | 8 | 2 | 3 | 7 | 5 | 2 |   | 8 | 8 | 2 |
| 125 | 7 | 6 | 6 | 2 | 7 | 7 | 9 | 7 | 1 |   | 5 | 2 |   |   | 7 | 7 |   |   |   |   |   |   | 6 | 4 |   |
|   |   |   |   |   |   |   |   |   | 5 | 4 | 7 | 8 | 4 | 8 | 8 | 9 | 7 | 6 | 4 | 7 | 2 | 7 | 8 | 8 | 8 |
| 126 |   |   |   |   |   |   |   |   | 1 |   |   |   |   |   | 4 | 2 |   |   |   |   |   |   | 2 |   |   |
|   |   |   |   |   |   |   |   |   | 5 |   | 4 | 7 | 2 | 7 | 8 | 8 | 6 |   | 2 | 2 |   |   | 2 | 7 | 7 |
| 127 | 6 | 5 | 7 | 4 |   | 7 | 8 | 6 | 1 | 2 | 1 | 8 | 1 | 2 | 8 | 8 | 4 | 2 | 1 | 4 |   |   | 8 | 8 | 4 |
|   |   |   |   |   |   |   |   |   | 5 |   |   | 2 |   |   | 8 | 8 | 2 |   |   | 2 |   |   | 7 | 6 | 2 |
| 128 | 5 | 7 | 7 | 6 |   | 8 | 8 | 2 | 1 | 7 | 5 | 8 | 3 |   | 8 | 8 | 2 | 6 | 6 | 8 | 4 |   | 8 | 7 | 2 |
|   |   |   |   |   |   |   |   |   | 5 | 2 | 2 | 2 |   |   | 8 | 8 |   | 5 | 4 | 7 | 2 |   | 8 | 6 |   |
| 129 | 7 | 5 | 7 | 6 | 5 | 7 | 6 | 5 | 1 | 7 | 7 | 8 | 5 | 8 | 8 | 9 | 8 | 7 | 7 | 7 | 4 | 6 | 7 | 8 | 4 |
|   |   |   |   |   |   |   |   |   | 5 | 2 | 6 | 7 | 4 | 8 | 8 | 6 |   | 2 | 2 | 2 | 2 |   | 6 | 7 | 2 |
| 130 | 8 | 8 | 7 | 6 | 8 | 8 | 8 | 8 | 1 | 8 | 8 | 8 | 8 | 8 | 9 | 9 | 8 | 8 | 9 | 7 | 6 | 8 | 8 | 8 | 6 |
|   |   |   |   |   |   |   |   |   | 5 | 5 | 8 | 8 | 5 | 8 | 8 | 9 | 8 | 4 | 7 | 4 | 5 | 4 | 8 | 6 | 5 |
| 131 |   |   | 4 | 2 |   | 8 | 8 | 5 | 1 |   |   | 5 | 2 | 7 | 8 | 8 | 7 | 2 | 4 | 3 | 2 |   | 7 | 7 | 5 |
|   |   |   |   |   |   |   |   |   | 5 |   |   | 2 |   | 2 | 8 | 7 | 6 |   |   | 2 |   |   | 7 | 5 | 4 |
| 132 | 6 | 7 | 6 | 7 | 7 | 7 | 8 | 5 | 1 | 5 | 7 | 8 | 2 | 6 | 8 | 8 | 6 | 4 | 8 | 7 | 4 | 7 | 8 | 8 | 5 |
|   |   |   |   |   |   |   |   |   | 5 | * | * | * | * | * | * | * | * | * | * | * | * | * | * | * | * |
| 139 | 8 | 6 | 8 | 6 | 6 | 7 | 5 | 8 | 1 | 8 | 6 | 8 | 7 | 7 | 8 | 8 | 8 | 7 | 9 | 8 | 7 | 8 | 7 | 8 | 8 |
|   |   |   |   |   |   |   |   |   | 5 | 7 | 4 | 7 | 6 | 6 | 8 | 6 | 7 | 5 | 8 | 7 | 5 | 5 | 7 | 8 | 7 |
| 140 | 3 | 7 | 6 | 7 | 7 | 8 | 4 | 7 | 1 | 7 | 7 | 8 | 6 | 8 | 8 | 8 | 7 | 7 | 9 | 5 | 6 | 8 | 8 | 8 | 8 |
|   |   |   |   |   |   |   |   |   | 5 | 5 | 4 | 8 | 5 | 8 | 8 | 8 | 6 | 3 | 4 | 3 | 2 | 7 | 8 | 8 | 8 |
| 141 | 7 | 8 | 7 | 2 | 8 | 8 | 8 | 8 | 1 | 6 | 7 | 7 | 4 | 8 | 9 | 9 | 9 | 6 | 7 | 8 |   | 8 | 8 | 8 | 9 |
|   |   |   |   |   |   |   |   |   | 5 | 5 | 5 | 7 | 2 | 8 | 8 | 8 | 8 | 5 | 6 | 6 |   | 6 | 8 | 8 | 9 |
| 142 | 8 | 8 | 8 | 6 | 7 | 8 | 8 | 8 | 1 | 8 | 8 | 8 | 6 | 8 | 8 | 8 | 8 | 5 | 8 | 8 | 7 | 8 | 8 | 8 | 8 |
|   |   |   |   |   |   |   |   |   | 5 | 6 | 8 | 8 | 5 | 7 | 8 | 8 | 8 |   | 7 | 7 | 6 | 8 | 8 | 8 | 7 |
| 143 | 8 | 8 | 6 | 4 | 7 | 8 | 7 | 7 | 1 | 8 | 8 | 8 | 2 | 8 | 9 | 8 | 8 | 7 | 8 | 3 | 2 | 7 | 8 | 8 | 8 |
|   |   |   |   |   |   |   |   |   | 5 | 8 | 7 | 8 | 2 | 8 | 8 | 7 | 8 | 2 | 4 | 2 | 1 | 5 | 8 | 7 | 5 |
| 144 | 7 | 7 | 6 | 5 | 2 | 8 | 4 | 8 | 1 | 7 | 8 | 8 | 6 | 7 | 8 | 8 | 7 | 7 | 8 | 7 | 4 | 5 | 8 | 8 | 8 |
|   |   |   |   |   |   |   |   |   | 5 | 4 | 8 | 8 | 5 | 7 | 8 | 8 | 7 | 6 | 7 | 6 | 2 | 4 | 8 | 8 | 8 |
| 145 | 6 | 5 | 4 | 6 | 5 | 7 | 4 | 6 | 1 | 6 | 7 | 8 | 5 | 7 | 8 | 8 | 5 | 4 | 4 | 4 | 2 | 3 | 8 | 8 | 6 |
|   |   |   |   |   |   |   |   |   | 5 | 5 | 7 | 7 | 4 | 7 | 8 | 8 | 4 | 4 | 2 | 2 |   |   | 7 | 8 | 5 |
| 146 | 7 | 7 | 8 | 6 | 8 | 8 | 9 | 7 | 1 | 7 | 7 | 8 | 4 | 8 | 9 | 8 | 7 | 8 | 8 | 8 | 4 | 8 | 8 | 8 | 7 |
|   |   |   |   |   |   |   |   |   | 5 | 6 | 5 | 8 | 1 | 7 | 8 | 7 | 7 | 6 | 7 | 6 | 2 | 6 | 8 | 7 | 7 |
| 147 | 7 | 7 | 8 | 6 | 8 | 8 | 8 | 7 | 1 | 7 | 7 | 8 | 2 | 8 | 8 | 8 | 8 | 8 | 9 | 8 | 7 | 8 | 8 | 8 | 8 |
|   |   |   |   |   |   |   |   |   | 5 | 4 | 6 | 7 | 2 | 7 | 8 | 8 | 7 | 4 | 8 | 6 | 5 | 6 | 8 | 7 | 7 |
| 148 | 8 | 8 | 7 | 7 | 8 | 8 | 8 | 7 | 1 | 8 | 7 | 8 | 6 | 8 | 9 | 9 | 8 | 8 | 9 | 8 | 7 | 8 | 8 | 8 | 8 |
|   |   |   |   |   |   |   |   |   | 5 | 6 | 6 | 8 | 2 | 8 | 8 | 8 | 7 | 6 | 8 | 8 | 5 | 7 | 8 | 8 | 7 |
| 149 | 8 | 7 | 8 | 7 | 8 | 8 | 8 | 7 | 1 | 7 | 7 | 9 | 8 | 8 | 9 | 9 | 8 | 7 | 9 | 8 | 6 | 6 | 7 | 7 | 5 |
|   |   |   |   |   |   |   |   |   | 5 | 7 | 7 | 8 | 7 | 8 | 8 | 8 | 7 | 7 | 8 | 7 | 6 | 6 | 7 | 7 | 4 |
| 150 | 6 | 7 | 7 | 6 | 8 | 8 | 8 | 7 | 1 | 6 | 5 | 9 | 7 | 8 | 8 | 8 | 8 | 8 | 8 | 7 | 7 | 6 | 7 | 7 | 7 |
|   |   |   |   |   |   |   |   |   | 5 | 4 | 2 | 7 | 6 | 8 | 8 | 8 | 7 | 7 | 7 | 6 | 7 | 5 | 7 | 7 | 7 |
| 151 | 7 | 6 | 7 | 6 | 7 | 8 | 8 | 7 | 1 | 4 | 6 | 8 | 6 | 7 | 8 | 8 | 7 | 8 | 7 | 6 | 2 | 8 | 8 | 8 | 8 |
|   |   |   |   |   |   |   |   |   | 5 | 2 | 2 | 7 | 5 | 7 | 8 | 8 | 7 | 5 | 2 | 5 |   | 7 | 8 | 8 | 7 |
| 152 | 7 | 6 | 7 | 5 | 6 | 8 | 7 | 6 | 1 | 7 | 7 | 9 | 7 | 7 | 8 | 8 | 8 | 7 | 8 | 7 | 6 | 5 | 6 | 7 | 4 |
|   |   |   |   |   |   |   |   |   | 5 | 6 | 6 | 8 | 6 | 7 | 8 | 8 | 6 | 5 | 7 | 6 | 4 | 5 | 7 | 7 | 2 |
| 153 | 7 | 7 | 6 | 7 | 7 | 8 | 8 | 6 | 1 | 7 | 7 | 8 | 6 | 8 | 8 | 9 | 8 | 7 | 5 | 7 | 5 | 4 | 6 | 5 | 2 |
|   |   |   |   |   |   |   |   |   | 5 | 5 | 7 | 7 | 5 | 8 | 7 | 7 | 7 | 6 | 4 | 6 | 4 |   | 5 | 2 |   |
| 159 | 7 | 7 | 6 | 5 | 4 | 7 | 4 | 6 | 1 | 8 | 8 | 9 | 8 | 8 | 8 | 8 | 8 | 8 | 9 | 7 | 4 | 7 | 8 | 8 | 8 |
|   |   |   |   |   |   |   |   |   | 5 | 6 | 8 | 8 | 7 | 7 | 8 | 8 | 7 | 2 | 7 | 5 | 2 | 2 | 8 | 8 | 7 |
| 160 | 8 | 8 | 8 | 7 | 8 | 8 | 9 | 7 | 1 | 7 | 7 | 8 | 7 | 8 | 8 | 8 | 8 | 9 | 9 | 8 | 9 | 8 | 8 | 8 | 8 |
|   |   |   |   |   |   |   |   |   | 5 | 7 | 7 | 8 | 7 | 8 | 7 | 8 | 7 | 8 | 8 | 8 | 4 | 7 | 8 | 8 | 8 |
| 161 | 7 | 7 | 8 | 6 | 8 | 8 | 9 | 7 | 1 | 7 | 7 | 8 | 6 | 8 | 8 | 9 | 8 | 8 | 8 | 9 | 4 | 7 | 8 | 9 | 9 |
|   |   |   |   |   |   |   |   |   | 5 | 6 | 6 | 7 | 5 | 8 | 8 | 8 | 7 | 7 | 6 | 8 | 2 | 6 | 8 | 8 | 7 |

What is claimed:

1. A compound of the formula

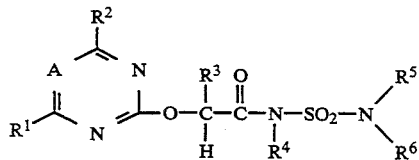

wherein

A is CR[7];

R[1], R[2], and R[7] are selected from the group consisting of hydrogen, halogen, formyl, cyano, carboxy, azido, alkyl, alkenyl, alkynyl, cycloalkyls, alkoxy, alkenylxoy, aryloxy, alkylthio, alkenylthio, alkynylthio, arylthio, alkylcarbonyl, alkoxy carbonyl, amino, aminoxy, and dialkyliminoxy groups;

R[3] is selected from the group consisting of hydrogen, alkyl, alkenyl, alkynyl, cycloalkyls, aralkyl, and aryl groups;

R[4] is selected from the group consisting of hydrogen, alkyl, alkenyl, alkynyl, and acyl groups of the formula COR[8] wherein R[8] is selected from the group consisting of alkyl, aralkyl, and aryl groups;

R[5] and R[6] are selected from the group consisting of hydrogen, alkyl, alkenyl, alkynyl, alkoxy, aryl, aralkyl, amino, cycloalkyls, heterocyclics, a group of the formula —SO$_2$R[8] wherein R[8] is a member of the group consisting of hydrogen, alkyl, alkenyl, alkynyl, alkoxy, aralkyl, amino, cycloalkyls, and heterocyclic groups; a group of the formula

wherein $R^{11}$ is an alkylthio group, and $R^5$ and $R^6$ may be taken together with the atom to which they are attached to form a group of the formula

wherein $R^9$ and $R^0$ are selected from the group consisting of alkyl, alkoxy, aryl, aralkyl, dialkylamine, and $R^9$ and $R^{10}$ may be taken together with the atom to which they are attached to form an aryl or heterocyclic group; or an agronomically acceptable salt thereof;

further wherein said alkyls of said compound are between $C_1$ and $C_{12}$, said alkenyls are between $C_2$ and $C_{12}$, said alkynyls are between $C_2$ and $C_{12}$, said cycloalkyls have between 3 and 8 ring members, said heterocyclic groups have between 5 and 6 ring members and are single ring systems, said heterocyclic groups further having one to three hetero atoms therein selected from the group consisting of oxygen, nitrogen, and sulphur, provided that one hetero atom is nitrogen and at most one oxygen or one sulfur; and said aryl groups are selected from the group consisting of single ring systems and fused ring systems, said aryl groups further having between 6 and 10 ring members.

2. The compound of claim 1, in which A represents CH.

3. The compound of claim 1, in which $R^1$ represents a $C_{1-4}$ alkyl, $C_{1-4}$ alkoxy, or $C_{1-4}$ haloalkyl group.

4. The compound of claim 3, in which $R^2$ represents a $C_{1-4}$ alkyl, $C_{1-4}$ alkoxy group or a halogen atom.

5. The compound of claim 4, in which $R^3$ represents a $C_{1-6}$ alkyl or a phenyl group.

6. The compound of claim 5, in which $R^4$ represents a hydrogen atom.

7. A compound of claim 6, in which $R^1$ is methyl, methoxy, or trifluoromethyl; $R^2$ is methyl, methoxy or chlorine; $R^3$ is methyl, ethyl, n-propyl, i-propyl, n-butyl, i-butyl, s-butyl, t-butyl or phenyl; $R^4$ is hydrogen; $R^5$ is hydrogen, methyl or ethyl; $R^6$ is hydrogen, methyl, ethyl, n-propyl, i-propyl, n-butyl, methoxy, chloroethyl, methoxycarbonylmethyl, mono- or di-methoxyethyl, allyl, propynyl, cyclopropyl, cyclobutyl, pyridyl, dimethylpyrimidinyl, (dichlorocyclopropyl)methyl, phenyl, chlorophenyl, or benzyl, or a group

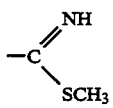

or $R^5$ and $R^6$ together are

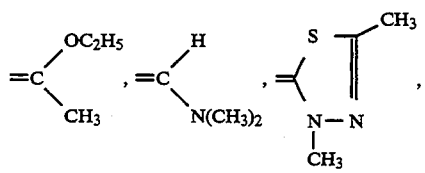

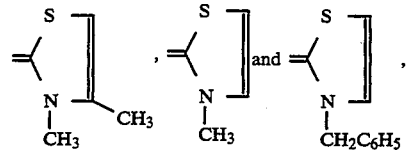

together are $-(CH_2)_2O(CH_2)_2-$, $-(CH_2)_2N(CH_3)(CH_2)_2-$ or $-(CH_2)_4-$.

8. The compound of claim 6 wherein $R^5$ and $R^6$ are selected from the group consisting of hydrogen, $C_{1-4}$ alkyl, $C_{1-4}$ haloalkyl, $C_{1-6}$ alkoxy, $C_{2-6}$ alkenyl, $C_{2-6}$ alkynyl, mono($C_{1-4}$ alkoxy)$C_{1-4}$ alkyl, di($C_{1-4}$ alkoxy)$C_{1-4}$ alkyl, ($C_{1-4}$alkoxy)carbonyl ($C_{1-4}$ alkyl), $C_{3-8}$cycloalkyl, benzyl, phenyl, pyridyl, pyrimidinyl, ($C_{3-8}$ cycloalkyl) $C_{1-4}$ alkyl, $R^5$ and $R^6$ may be taken together with the atom to which they are attached to form a group having the formula

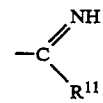

wherein $R^{11}$ is $C_{1-4}$ alkylthio, $R^5$ and $R^6$ may be taken together with the atom to which they are attached to form a group having the formula

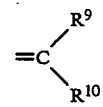

wherein
$R^9$ and $R^{10}$ are selected from the group consisting of $C_{1-4}$ alkyl, $C_{1-4}$ alkoxy, di($C_{1-4}$ alkyl)amino, and $R^9$ and $R^{10}$ may be taken together with the atom to which they are attached to form a 5 membered ring having 2 to 3 hetero atoms selected from the group consisting of nitrogen and sulphur, provided that one hetero atom is nitrogen and at most one sulfur, and wherein said ring is optionally substituted with $C_{1-4}$ alkyl.

9. The compounds of claim 1 wherein said salts are selected from the group consisting of agronomically acceptable salts with inorganic cations derived from alkali metals, alkaline earth metals and transition metals, and salts with organic cations.

10. The compounds of claim 9 wherein said cations are selected from the group consisting of sodium, potassium, calcium, magnesium, copper, alkylammonium and alkylsulfonium.

11. The compounds of claim 1 wherein said heterocyclic groups are selected from the group consisting of morpholino, piperazino, piperidino, pyrrolidino, pyridyl, pyrimidinyl, triazinyl, thiazolo, and thiadiazolo.

12. A herbicidal composition comprising a compound of claim 1 combined with a member of the group consisting of carriers, surface-active agents, and mixtures of carriers and surface-active agents.

13. A method of combatting undesired plant growth at a locus, which comprises treating the locus with a member of the group consisting of the compound of claim 1, a combination of the compound of claim 1 together with a carrier, a combination of the compound of claim 1 together with a surface-active agent, and a mixture of the compound of claim 1, surface-active agent, and carrier.

* * * * *